(12) United States Patent
Martin

(10) Patent No.: US 9,675,065 B2
(45) Date of Patent: Jun. 13, 2017

(54) BIOCIDE AND BLEACH COMPOSITIONS AND RELATED METHODS

(71) Applicant: Roy Martin, Downers Grove, IL (US)

(72) Inventor: Roy Martin, Downers Grove, IL (US)

(73) Assignee: TRUOX, INC., McClellan, CA (US)

(*) Notice: Subject to any disclaimer, the term of this patent is extended or adjusted under 35 U.S.C. 154(b) by 208 days.

(21) Appl. No.: 14/154,451

(22) Filed: Jan. 14, 2014

(65) Prior Publication Data

US 2015/0196027 A1 Jul. 16, 2015
US 2017/0105412 A9 Apr. 20, 2017

Related U.S. Application Data

(60) Division of application No. 13/347,854, filed on Jan. 11, 2012, now abandoned, which is a continuation-in-part of application No. 13/066,226, filed on Apr. 8, 2011, now abandoned, and a continuation-in-part of application No. 13/066,199, filed on Apr. 8, 2011, now abandoned, said application No. 13/066,226 is a continuation-in-part of application No. 12/932,469, filed on Feb. 25, 2011, now abandoned, which is a continuation-in-part of application No. 12/931,896, filed on Feb. 14, 2011, now abandoned.

(51) Int. Cl.
*A01N 37/02* (2006.01)
*C02F 1/50* (2006.01)
*A23L 3/3544* (2006.01)
*A01N 43/08* (2006.01)
*A23L 3/3517* (2006.01)
*A01N 59/00* (2006.01)
*C02F 103/00* (2006.01)

(52) U.S. Cl.
CPC ............. *A01N 37/02* (2013.01); *A01N 43/08* (2013.01); *A01N 59/00* (2013.01); *A23L 3/3517* (2013.01); *A23L 3/3544* (2013.01); *C02F 1/50* (2013.01); *C02F 2103/002* (2013.01)

(58) Field of Classification Search
CPC ........ A01N 37/02; A01N 43/08; A01N 59/00; A23L 3/3517; A23L 3/3544; C02F 1/50; C02F 2103/002; C02F 2303/04; A23V 2002/00
See application file for complete search history.

(56) References Cited

U.S. PATENT DOCUMENTS

| | | | |
|---|---|---|---|
| 2,482,891 A | 9/1949 | Royden Aston | |
| 3,671,629 A | 6/1972 | Levy | |
| 4,129,517 A | 12/1978 | Eggensperger | |
| 4,671,972 A | 6/1987 | Schobel | |
| 5,525,121 A | 6/1996 | Heffner | |
| 5,688,515 A | 11/1997 | Kuechler | |
| 5,755,993 A | 5/1998 | Heffner | |
| 5,801,116 A | 9/1998 | Cottrell | |
| 5,965,264 A | 10/1999 | Barenberg | |
| 6,096,348 A | 8/2000 | Miner | |
| 6,319,888 B2 | 11/2001 | Wei | |
| 6,384,006 B1 | 5/2002 | Wei | |
| 6,569,353 B1 | 5/2003 | Giletto | |
| 6,699,404 B2 | 3/2004 | Speronello | |
| 6,866,870 B2 | 3/2005 | Day | |
| 7,150,854 B2 | 12/2006 | Koermer | |
| 7,182,883 B2 | 2/2007 | Speronello | |
| 7,354,604 B2 | 4/2008 | Ramirez | |
| 7,915,207 B2 | 3/2011 | Hertdt | |
| 7,935,667 B2 | 5/2011 | Tichy | |
| 2001/0012504 A1 | 8/2001 | Thangaraj | |
| 2002/0155067 A1 | 10/2002 | McGregor | |
| 2003/0080317 A1 | 5/2003 | Speronello | |
| 2003/0180384 A1 | 9/2003 | Koermer | |
| 2005/0113279 A1 | 5/2005 | Desmarescaux | |
| 2005/0235830 A1* | 10/2005 | Hughes | A01N 59/00 96/108 |
| 2011/0014276 A1 | 1/2011 | Karagoezian | |
| 2012/0207858 A1* | 8/2012 | Martin | A01N 59/00 424/661 |

FOREIGN PATENT DOCUMENTS

| | | |
|---|---|---|
| EP | 1902119 B1 | 3/2011 |
| WO | 2007008478 A1 | 1/2007 |
| WO | 2007078838 A1 | 7/2007 |
| WO | 2007131970 | 11/2007 |

OTHER PUBLICATIONS

1988 Russ. Chem. Rev. 57 1041, Titled The Synthesis and Properties of Covalent Organic Perchlorates.
Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2).
A.O.A.C. Use Dilution Methods, Official Methods of Analysis of the Association of Official Analytical Chemists, paragraph 955.14 and applicable sections, 15th Edition, 1990 (EPA Guideline 91-2).
Rufina Alamo, et. al.,"Polymerization of Tetrahydrofuran by Bifunctional Cationic Initiators: Terephthaloyl Perchlorate," Chem. 182, pp. 731-737 (1981).
Yu. Nikolyukin, et. al., "Synthesis of Funcationally Substituted Benzo(c)pyrylium Salts," Chemistry of Heterocyclic Compounds, vol. 26, Issue 4, Apr. 1990, pp. 397-402.

\* cited by examiner

*Primary Examiner* — Sarah Pihonak
*Assistant Examiner* — Jason A Deck
(74) *Attorney, Agent, or Firm* — Jeffrey S. Melcher; Manelli Selter PLLC

(57) ABSTRACT

Provided are biocide compositions and bleach compositions comprising organic acyl polyoxychlorine and related methods. The reduction of the acyl polyoxychlorine group releases a reactive intermediate that undergoes a series of cascading reduction steps, resulting in termination products Generally Recognized As Safe.

12 Claims, 10 Drawing Sheets

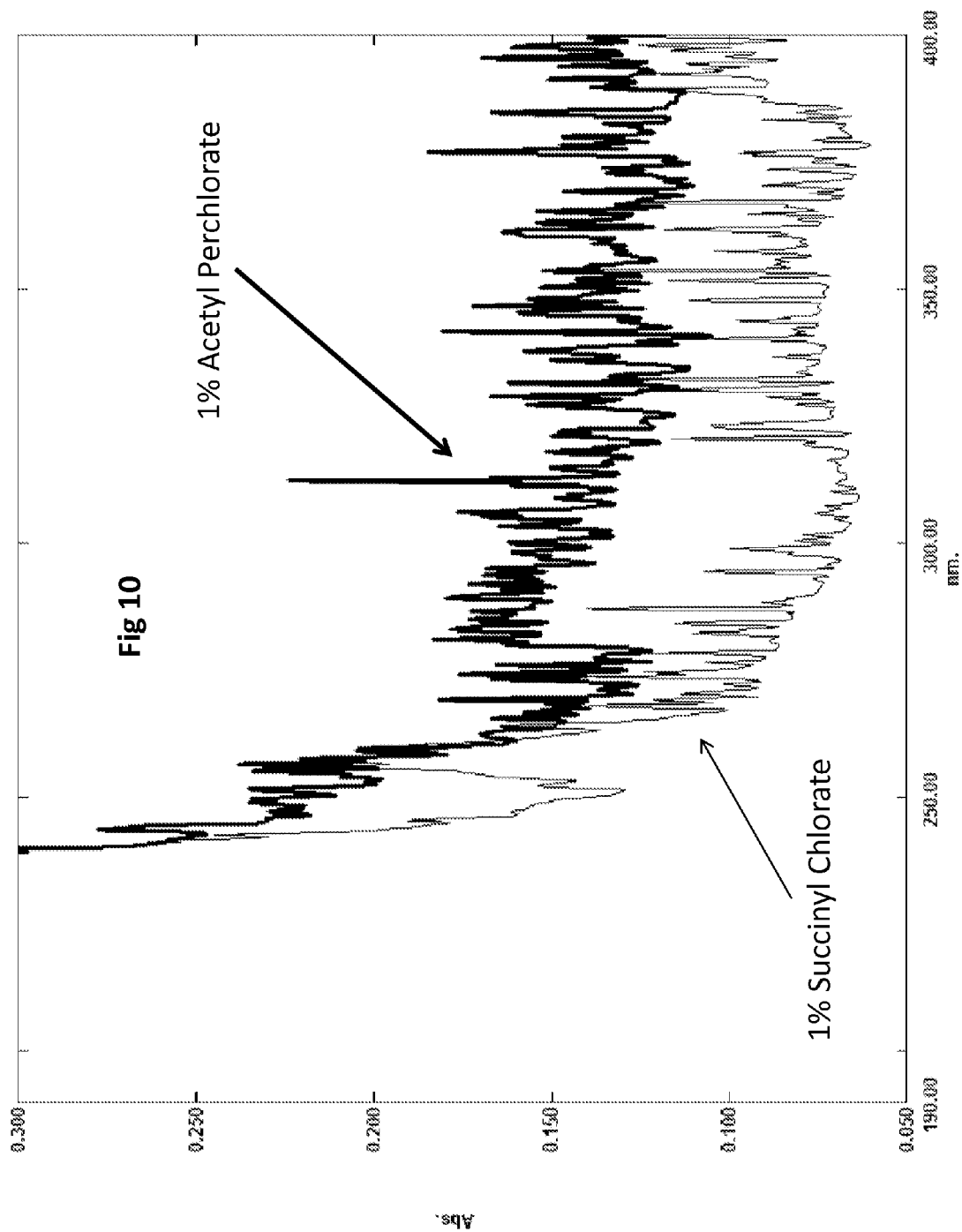

BIOCIDE AND BLEACH COMPOSITIONS AND RELATED METHODS

RELATED APPLICATIONS

This application is a Continuation-in-Part (CIP) of U.S. patent application Ser. No. 13/066,226 filed on 8 Apr. 2011, which is a Continuation-in-Part (CIP) of U.S. patent application Ser. No. 12/932,469 filed on 25 Feb. 2011, which is a Continuation-in-Part (CIP) of U.S. patent application Ser. No. 12/931,896 filed on 14 Feb. 2011. This application is a Continuation-in-Part (CIP) of U.S. patent application Ser. No. 13/066,199 filed on 8 Apr. 2011. The entire content of these patent applications are incorporated by reference herein.

FIELD OF INVENTION

The present invention relates to biocide compositions, methods for killing microorganisms, bleach compositions, and methods of bleaching.

BACKGROUND

Organic alkyl perchlorates are reported to have been used in polymerization reactions for years. Organic alkyl perchlorates are powerful oxidizers that are known to be extremely hazardous, and are effective alkylating agents.

With reference to the publication "1988 Russ. Chem. Rev. 57 1041", Titled "The Synthesis and Properties of Covalent Organic Perchlorates".

Numerous methods for producing organic alkyl perchlorates are reviewed. Common methods discussed in the referenced paper include reacting alcohols with perchloric acid under tightly controlled temperatures to form perchloric acid mono and poly esters. However, the resulting organic perchlorates are oil based, and when contacted with dilute amounts of water decompose resulting in an "enormously powerful explosions".

Furthermore, the reference discloses cyclic ethers including epoxides can be reacted with chlorine heptoxide in an organic solvent at 0° C. to produce diperchlorates.

Biocide compositions are commonly used for the treatment of recirculating systems such as industrial cooling systems and swimming pools, disinfecting hard surfaces, food intervention, disinfecting food processing equipment, sterilizing surgical instruments and the like.

Chlorine dioxide is an oxychlorine compound that is an effective oxidizing biocide that is currently approved for use in these types of application.

In order to obtain sporicidal registration through the U.S. EPA and FDA, meeting the requirements of AOAC method 966.04 is necessary. The AOAC method 966.04 is considered to be one of the most if not the most difficult test to meet due to the nature of the test. *C. Sporogenes* and *B. Subtilis* spores are affixed to ceramic cylinders in a proteinaceous and soil based matrix. This matrix is difficult to penetrate and as a result, otherwise extremely effective biocides such as chlorine dioxide and peracetic acid can require as much as 1 hour or more of contact time with 1000 ppm as $ClO_2$ to meet the requirements for being sporicidal using AOAC method 966.04.

Furthermore, at such high concentrations of $ClO_2$ needed to meet the criteria for being regarded as a sporicidal, the high volatility of chlorine dioxide can be a significant issue and health concern.

There is a need for a fast acting biocide composition that can provide the benefits of chlorine dioxide without its limitations, while improving penetration of biofilms, proteinaceous deposits and accelerate inactivation of microbiological organisms including *mycobacterium*, spores, and oocyst at an accelerated rate. There is also a need for broad-spectrum bleach that can be applied to colored clothing, fabrics, and various surfaces without damage to the dye and corrosion while effectively oxidizing the chromophores of the stain.

A chromophore is the part of a molecule responsible for its color. The color arises when a molecule absorbs certain wavelengths of visible light and transmits or reflects others. The chromophore is a region in the molecule where the energy difference between two different molecular orbitals falls within the range of the visible spectrum. Visible light that hits the chromophore can thus be absorbed by exciting an electron from its ground state into an excited state.

In the conjugated chromophores, the electrons jump between energy levels created by a series of alternating single and double bonds, often in aromatic systems. Common examples include various food colorings, fabric dyes (azo compounds), pH indicators, lycopene, β-carotene, and anthocyanins. Various factors in a chromophore's structure go into determining at what wavelength region in a spectrum the chromophore will absorb. Lengthening or extending a conjugated system with more unsaturated (multiple) bonds in a molecule will tend to shift absorption to longer wavelengths.

The metal complex chromophores arise from the binding of a transition metal to ligands. Examples of such chromophores can be seen in chlorophyll (used by plants for photosynthesis), hemoglobin, hemocyanin, and colorful minerals such as malachite and amethyst.

Paper pulp comprises lignin which is a chromophore that binds the cellulose of wood fiber together. Residual lignin in paper imparts an undesirable color and acidity to the paper. Bleaching is used to break the lignin ring thereby freeing the cellulose and whitening the cellulose for use in paper.

Clothing is often stained with undesirable chromophores that are difficult to remove during laundering. Sources of well known chromophores that stain clothing include tomato juice, wine, grape juice, grass stains, blood and the like.

There is a need for an effective, fast acting and environmentally friendly color-safe bleach that can facilitate the oxidation of chromophores without damaging the fabric of laundry, cellulose of paper pulp, and does not form undesirable decomposition byproducts like dioxin.

The present invention meets these and other needs in a unique and highly facile way.

U.S. Pat. No. 6,866,870 ("870") discloses a biocide composition formed from ingredients comprising peroxide and a hypochlorite, wherein the biocide composition is formed by adding the peroxide ingredient to the hypochlorite ingredient so that the weight ratio of the hypochlorite to the peroxide is in the range of 10:1 to 100:1.

The "870" patent is very limited in that: the peroxide ingredient must be added to the hypochlorite ingredient in a specific sequence; the method of producing the biocide composition requires a two-component system (bi-component); the biocide composition cannot be a solid composition; and the weight ratio of hypochlorite to peroxide must be at least 10:1, and the method of producing a biocide composition must be carried out in essentially the absence of organic matter, thereby eliminating the use of organic acids, anhydrides, surfactants and the like.

U.S. Patent Application No. 2011/0014276 A1 discloses an antimicrobial preservative for use in an ophthalmic product, the preservative comprising from 0.005 wt. % to 0.20 wt. % chlorite compound and from 0.005 wt. % to 0.05 wt. % peroxy compound, wherein the preservative does not generate chlorine dioxide, and wherein the preservative is at a pH range between 6.0 and 8.8.

U.S. Pat. No. 2,482,891 discloses a solid composition comprising an acid anhydride and alkali and alkali earth metal chlorite for producing chlorine dioxide.

U.S. Pat. No. 6,096,348 discloses a disinfectant and/or sterilant comprising from 1 to 30% hydrogen peroxide and a carboxylic acid and carboxylate salt.

U.S. Pat. No. 7,354,604 discloses a disinfectant solution comprising 2-furoic acid and hydrogen peroxide.

SUMMARY OF THE INVENTION

The present invention is based on the discovery of a new oxidizer that comprises organic acyl polyoxychlorine compounds. It has been discovered that these new compounds are a form of "sequestered chlorine dioxide" that provide excellent stability and a surprisingly high level of antimicrobial and bleaching efficacy. These powerful oxidizing compounds were found to be unexpectedly stable in an aqueous solution under a wide range of pH, in the presence of organic based additives, and in the presence of organic based contaminants that compromise other oxidizing biocides. The discovery of organic acyl polyoxychlorine compounds brings to light a new generation of efficient and environmentally friendly biocide compositions and bleaches that result in the formation of chlorine dioxide and terminate with end products that are environmentally benign or Generally Recognized As Safe (GRAS).

The organic acyl polyoxychlorine compounds of the invention provide numerous advantages over percarboxylic acids, chlorous acid, chlorine dioxide, hypochlorites, and other commonly used oxidizing biocides and bleaches. Examples of benefits include but are not limited to: reduction of the organic acyl polyoxychlorine compounds consume 7 to 9 electrons depending on whether the polyoxychlorine comprises a chlorate or perchlorate anion respectively, thereby greatly increasing efficiency; high stability in the presence of many organics increases survivability in antimicrobial applications; the organic acyl donor can be selected so the decomposition of the organic acyl polyoxychlorine compounds results in termination products that are Generally Recognized as Safe; the organic acyl polyoxychlorine compounds, once produced, are stable over a broad pH range; solid forms of organic acyl polyoxychlorine may be produced; the organic portion of the organic acyl polyoxychlorine can be selected to increase the molecules lipophilicity to increase permeation through the cell membranes of microbiological organisms; excellent self-life under a broad range of pH and organic additives; and low volatility.

BRIEF DESCRIPTION OF THE FIGURES

FIG. 6—illustrates the UV spectrum for 1% peracetic acid and 10% hydrogen peroxide during reduction. The observed peaks are associated with various oxygen species exemplified by oxygen, singlete oxygen, hydroxyl radicals, superoxide and the like.

FIG. 2 illustrates the termination product resulting from the reduction of succinyl chlorate has a UV spectrum comparable to the parent organic acid, in this illustration succinic acid.

FIG. 10—compares the UV spectrum for 1% succinyl chlorate to 1% acetyl perchlorate during their chemical reduction. The UV spectrum illustrates the higher energy from the perchlorate based organic acyl polyoxychlorine compared to the chlorate based organic acyl polyoxychlorine, however both chlorate and perchlorate based organic acyl polyoxychlorine compounds produce oxychlorine intermediates comprising at least chlorine dioxide and chlorite.

DEFINITIONS

Figure 1:
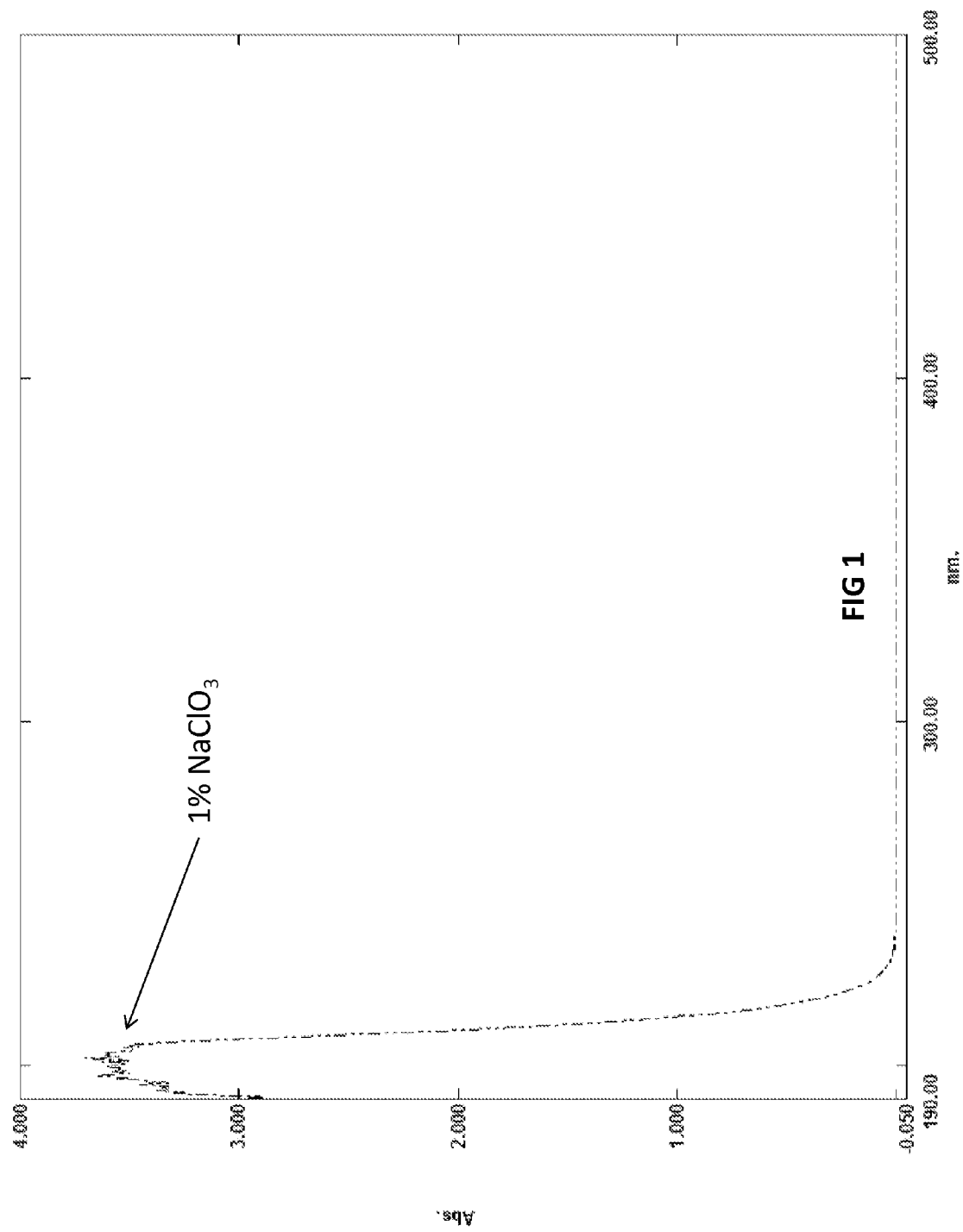
FIG. 1—illustrates the UV spectrum for a 1% solution of sodium chlorate in distilled water.
Figure 2:
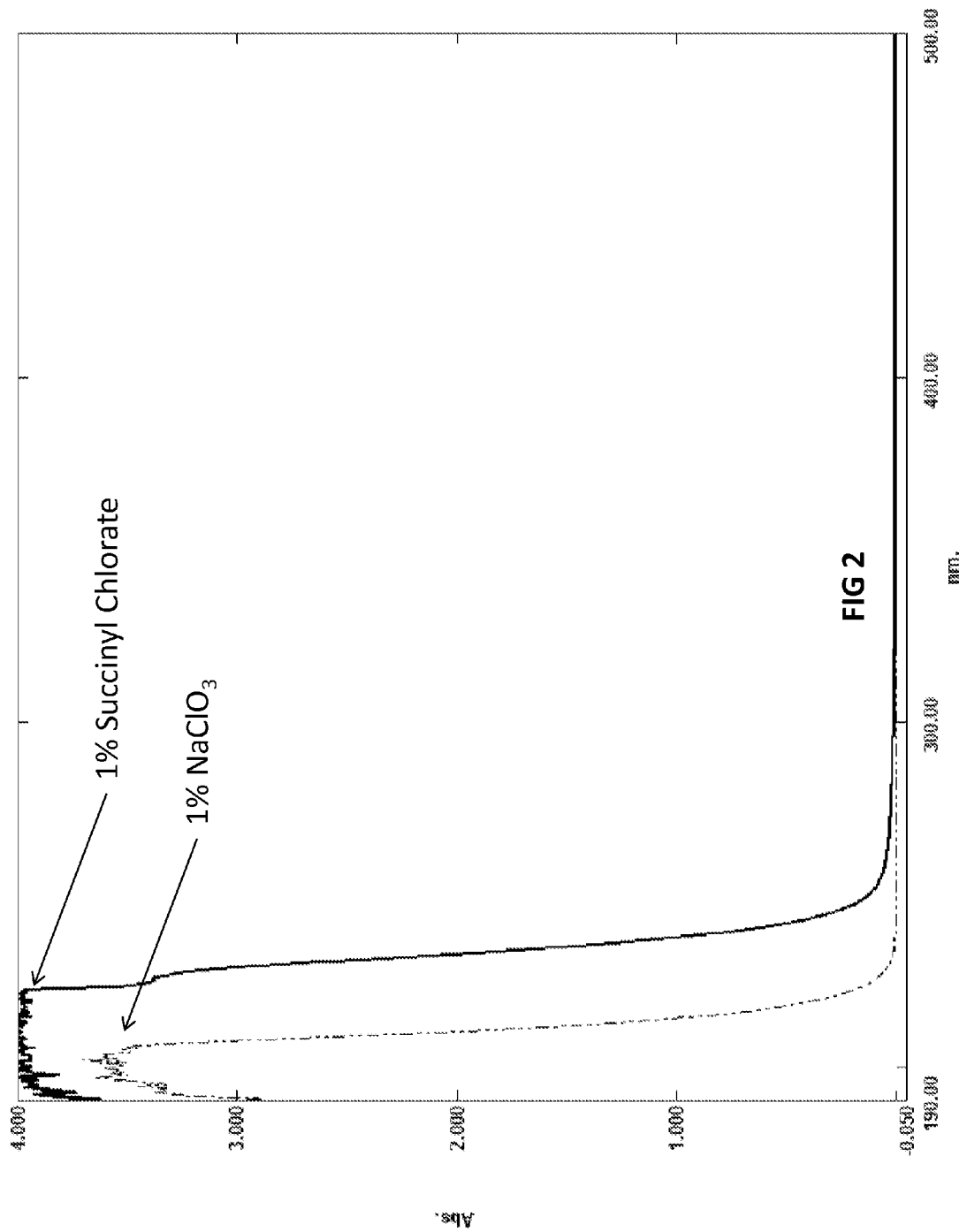
FIG. 2—illustrates the UV spectrum for a 1% solution of succinyl chlorate resulting from the reaction between succinic anhydride with sodium chlorate in an acid pH aqueous solution.
Figure 3:
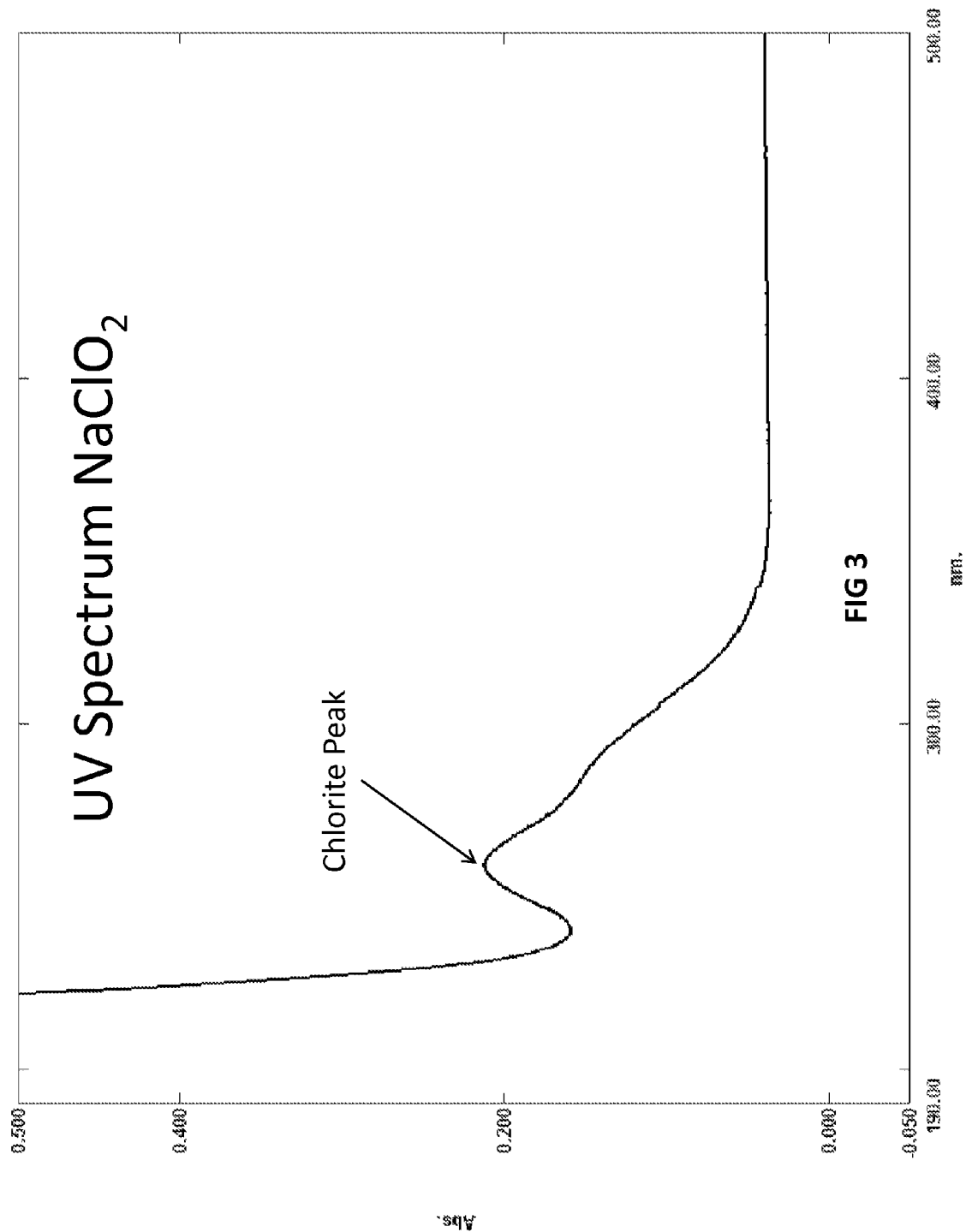
FIG. 3—illustrates the UV spectrum and characteristic peak of sodium chlorite dissolved in distilled water.
Figure 4:
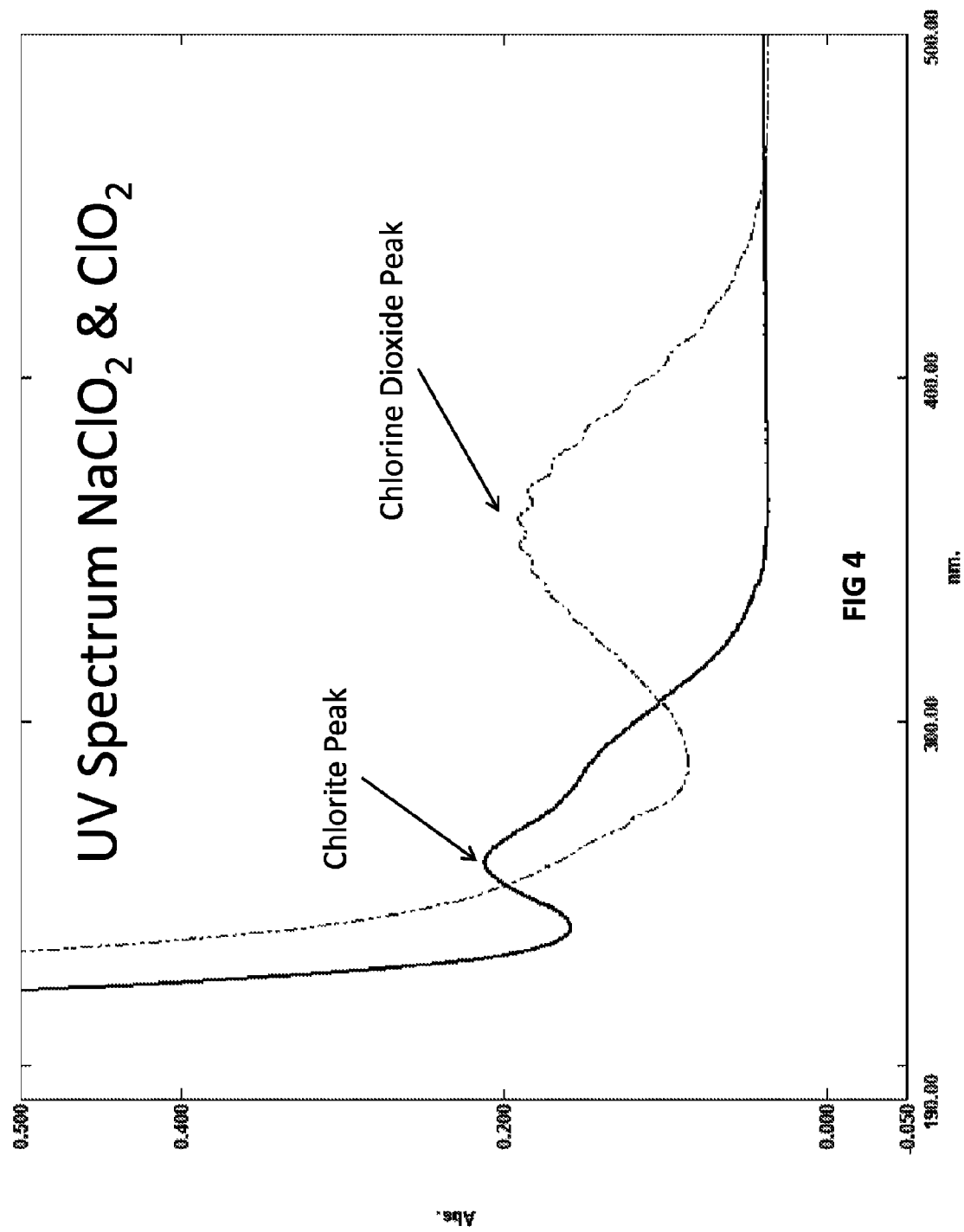
FIG. 4—illustrates the UV spectrum and characteristic peak of chlorine dioxide compared to sodium chlorite.
Figure 5:
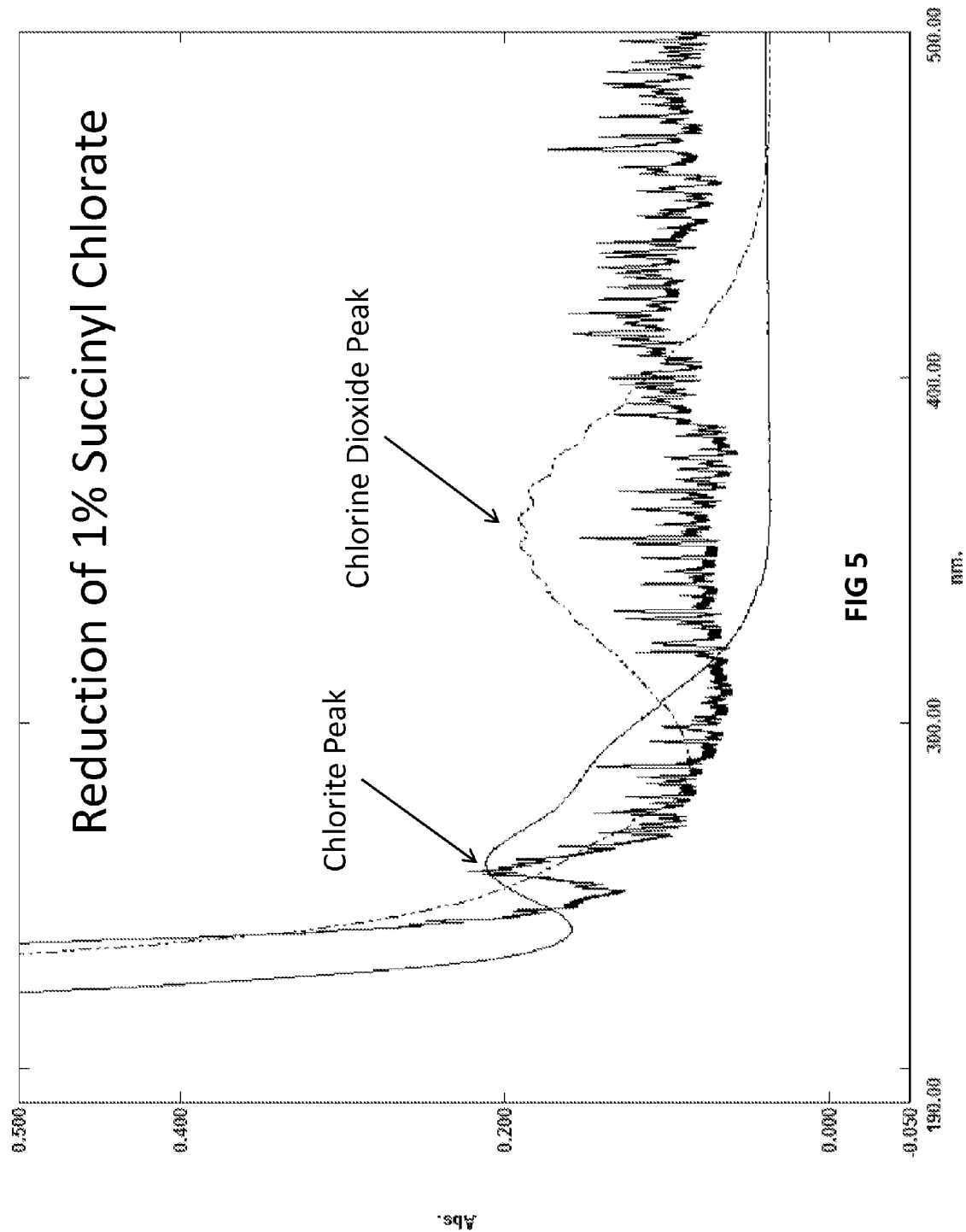
FIG. 5—illustrates the UV spectrum of 1% succinyl chlorate undergoing reduction, and compares the characteristic peaks of sodium chlorite and chlorine dioxide to those produced during the cascading reduction of succinyl chlorate. The formation of various oxychlorine intermediates during the cascading reduction steps results in formation of various intermediates that forms additional peaks not observed in UV spectrum of relatively pure or specific reagents such as sodium chlorite and chlorine dioxide.
Figure 6:
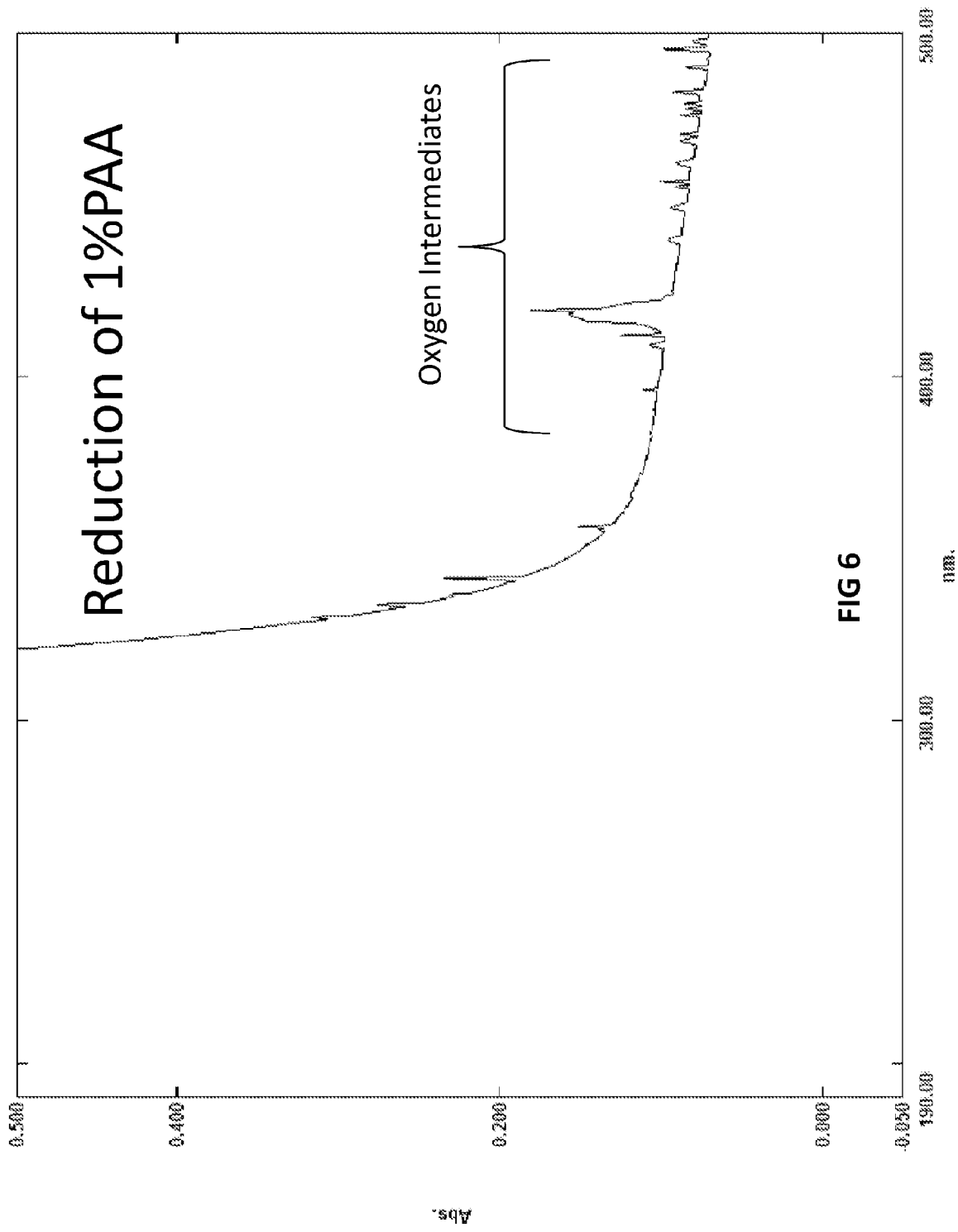
Figure 7:
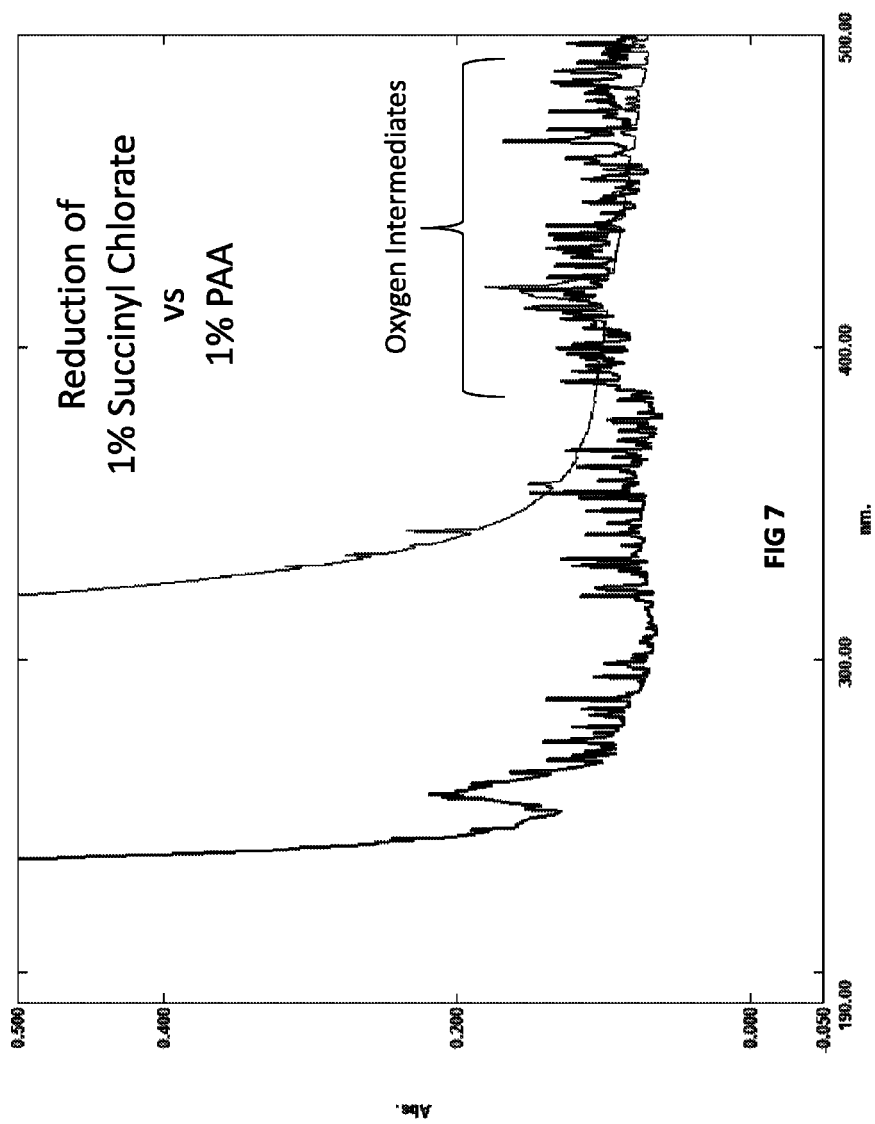
FIG. 7—illustrates a comparison between the UV spectrum resulting from reduction of 1% succinyl chlorate and reduction of 1% peracetic acid. Almost a perfect overlay occurs at approximately 420 nm, however, 1% succinyl chlorate demonstrates higher magnitude peaks over a much broader region of the UV spectrum.
Figure 8:
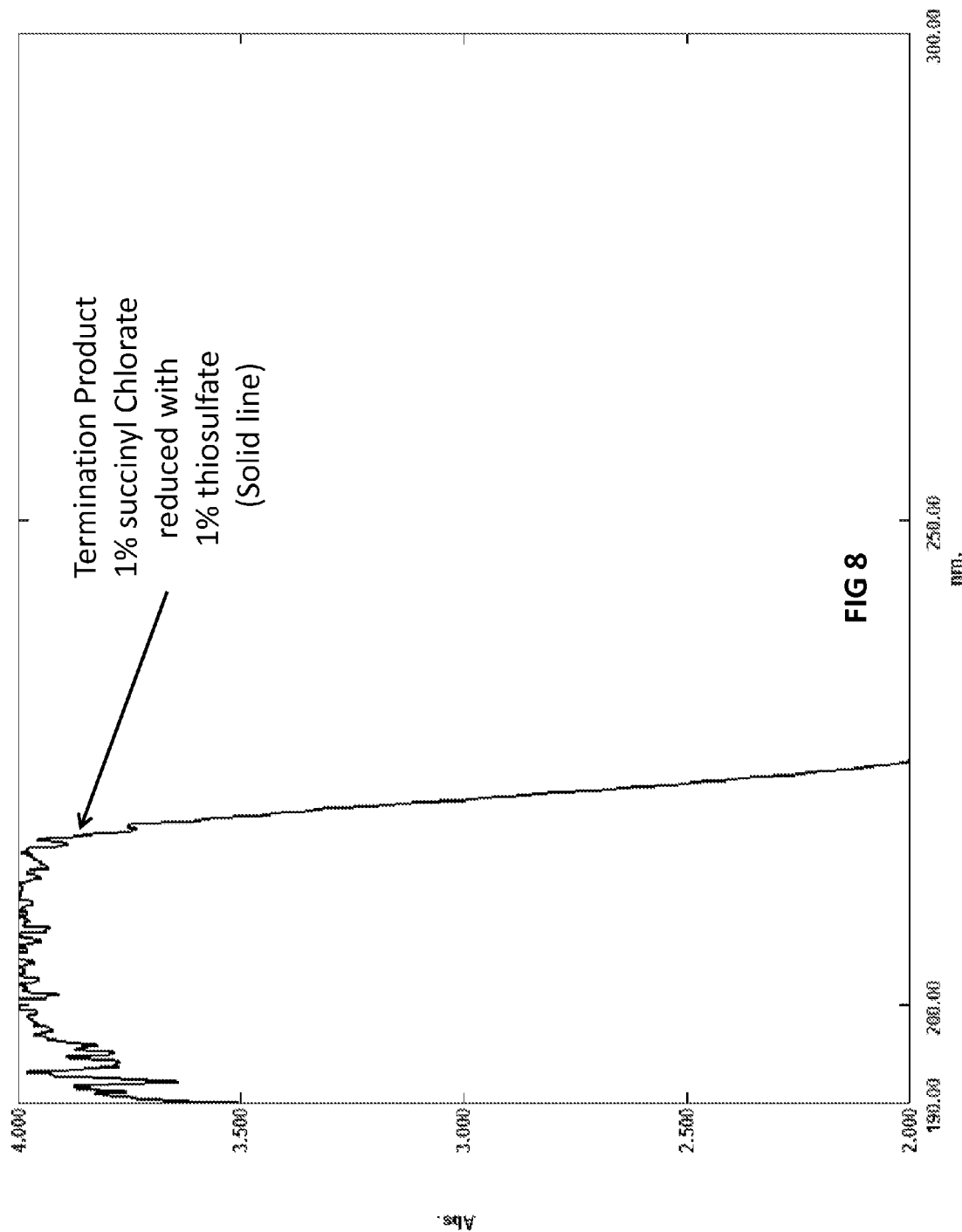
FIG. 8—illustrates the UV spectrum of the termination products resulting from the reaction between 1% succinyl chlorate and 1% sodium metabisulfite.
Figure 9:
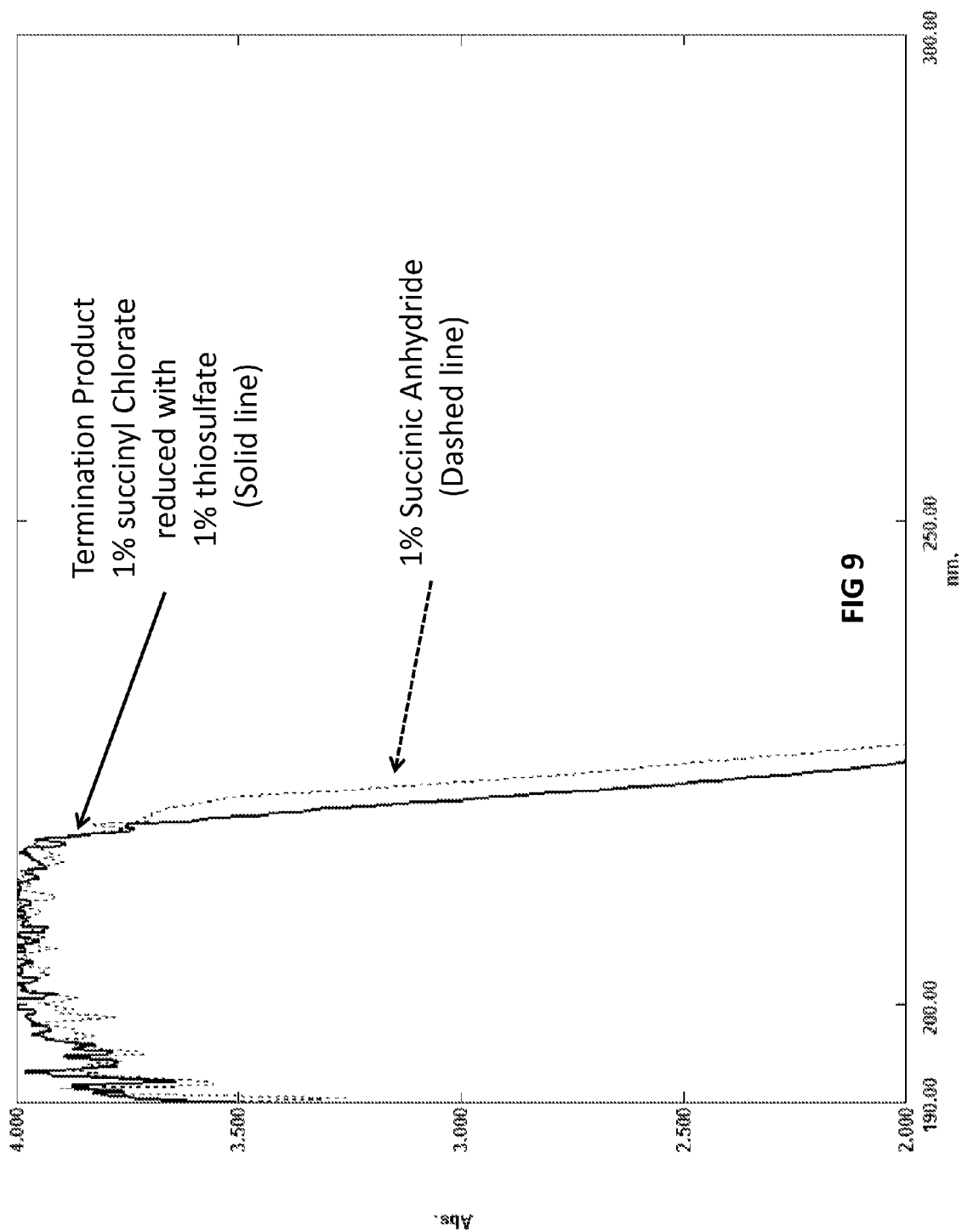
FIG. 9—illustrates an overlay comparing the termination products resulting from the reduction of 1% succinyl chlorate by 1% sodium metabisulfite (solid line in FIG. 8), and the UV spectrum of 1% succinic anhydride dissolved in distilled water. The UV spectrum of the succinic anhydride is representative of succinic acid as the succinic anhydride hydrolyses in water to form succinic acid. The data, compared to FIG. 1

As used herein, "sequestered chlorine dioxide" describes an organic acyl polyoxychlorine compound that produces chlorine dioxide as one of the oxychlorine intermediates resulting from the chemical reduction of the acyl polyoxychlorine group.

The organic acyl polyoxychlorine compound having the general formula:

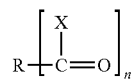

wherein (X) comprises a polyoxychlorine selected from at least one chlorate having the general formula $ClO_3$ and perchlorate having the general formula $ClO_4$;

(R) comprises hydrogen or a $C_1$ to $C_{23}$ primary carbon based structure; and where (n) is one or more acyl polyoxychlorine groups. Alternatively, (R) can defined as a backbone for the acyl polyoxychlorine compound. The backbone can be a hydrocarbon comprising at least one carbon and at least one hydrogen or a substituted hydrocarbon comprising at least one carbon, at least one hydrogen, and at least one other element from the Periodic Table of Elements.

As used herein, "primary carbon based structure" is that carbon based chain of the organic polyoxychlorine compound having the greatest length of carbon atoms and directly appending the acyl polyoxychlorine group. The primary carbon based structure comprises an: alkyl, arylalkyl, cycloalkyl, aromatic, or heterocyclic group. The primary carbon based structure can be saturated or unsaturated as well as substituted or unsubstituted. The primary carbon based structure (R) may be substituted with moiety exemplified by: amino, amide, sulfonate, carboxylate, alkoxylate, hydroxyl, carbonyl, and phosphonate. The primary carbon based structure is referred to in the general structure as (R).

As used herein, "activated" refers to the activation of organic acyl polyoxychlorine. Activation occurs as a result of combining at least two components, one component acidified, the second component buffered with a carbonate based alkalinity. The activation occurs when the two components are combined in a manner that results in release of carbon dioxide gas. The method is non-limiting in sense that the component comprising the organic acyl polyoxychlorine can be the acidified component, or the buffered component. Non-limiting examples of sources of carbonate based alkalinity include sodium bicarbonate ($NaHCO_3$) and sodium carbonate ($Na_2CO_3$).

As used herein, "acyl polyoxychlorine group" comprises an organic acyl group wherein the acyl carbon atom is bonded to an oxygen atom which is bonded to the chlorine atom, and where the chlorine atom has from 2 to 3 additional oxygen atoms bonded to it.

As used herein, "oxychlorine intermediate" comprises the oxychlorine compounds resulting from the initial reduction of the acyl polyoxychlorine group, and the subsequent oxychlorine compounds resulting from the reduction of the oxychlorine intermediate. The oxychlorine intermediate is the reactive leaving group released from the organic acyl polyoxychlorine compound when the organic acyl polyoxychlorine compound undergoes reduction, as well as any chlorine-oxygen based intermediates that result during the reduction of the oxychlorine intermediates. For example, when an acyl polyoxychlorine group resulting from reaction of a chlorate anion with an organic acyl donor undergoes chemical reduction, the resulting oxychlorine intermediates comprise at least chlorine dioxide and chlorite.

As used herein, "organic acyl donor" comprises organic based compounds that result in formation of organic acyl polyoxychlorine compounds when reacted with a polyoxychlorine anion. Examples of organic acyl donors include carboxylic acids, and carboxylic acid derivatives exemplified by acyl chlorides (RCOCl), acid anhydrides ($RCO_2COR$), esters ($RCO_2R$), amides ($RCONH_2$), and salts of carboxylic acids.

As used herein, "polyoxychlorine anions" refers to the production of the organic acyl polyoxychlorine compounds. Polyoxychlorine anions comprise chlorate anions and perchlorate anions having the general formulas $ClO_3^-$ and $ClO_4^-$ respectively.

As used herein, "polyoxychlorine" refers to the general formula of the organic acyl polyoxychlorine compound and comprises at least one of chlorate having the general formula $ClO_3$ and perchlorate having the general formula $ClO_4$. The polyoxychlorine is bonded to the acyl carbon atom of the organic acyl group.

As used herein, "polyoxychlorine anion donors" comprise: hydrogen, ammonium, alkali and alkali earth metal chlorate ($ClO_3^-$); and, hydrogen, ammonium, alkali and alkali earth metal perchlorate ($ClO_4^-$). Specific non-limiting examples include but are not be limited to: chloric acid, ammonium chlorate, lithium chlorate, sodium chlorate, potassium chlorate, magnesium chlorate, calcium chlorate, perchloric acid, ammonium perchlorate, lithium perchlorate, sodium perchlorate, potassium perchlorate, magnesium perchlorate, calcium perchlorate.

As used herein, "water" refers to any media that comprises at least some proportion of water having the general formula $H_2O$. The bleach and biocide compositions comprising organic acyl polyoxychlorine and water are not limited to water in its pure form $H_2O$. Water also refers to water used as a means of dilution of biocide and bleach compositions. Water also refers to systems or applications comprising mostly $H_2O$ exemplified by recirculating cooling tower systems.

As used herein, the term "aqueous solution" means the solution comprises at least some portion of water having the general formula $H_2O$. Aqueous solutions may further include significant proportions of other solvents exemplified by alcohols, dimethyl sulfoxide (DMSO), acetone, ethyl acetate, as well as other additives exemplified by surfactants, dispersants, sequestrants, chelants, oxidizers such as hydrogen peroxide and peracids, colorants, perfumes, viscosity modifiers and the like. An aqueous solution may also be an emulsion, a suspension, or a hydrogel.

As used herein, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

As used herein, "chemical reduction" or "reduction" refers to organic acyl polyoxychlorine and subsequent oxychlorine intermediates undergoing chemical reactions resulting in a gain of electrons. One non-limiting example is chemical reduction of acetyl chlorate resulting in the formation of acetic acid and chlorine dioxide.

As used herein, "cyclic anhydride" describes compounds comprising two organic acyl groups bound to a common oxygen atom and having a common carbon based backbone comprising 2 to 6 carbon atoms. Specific non-limiting examples of cyclic anhydrides include but are not be limited to succinic anhydride, methyl succinic anhydride, ethyl succinic anhydride, glutaric anhydride, adipic anhydride, maleic anhydride, pimelic anhydride, phthalic anhydride, suberic anhydride and the like. The carbon based backbone may include substituted branches as illustrated by methyl succinic anhydride and ethyl succinic anhydride. The carbon based backbone does not limit the cyclic anhydride structure to a simple chain of 2 to 6 carbon atoms.

As used herein, "terminating carboxylic acid" is the terminating organic carboxylic acid (or its carboxylate salt) resulting from the chemical reduction of the organic acyl polyoxychlorine compound. For example, the reduction of octanoyl chlorate results in the formation of the terminating carboxylic acid octanoic acid or its octanoate salt depending on pH.

As used herein, "alkalinity donor" consumes hydrogen ions, thereby inducing an increase in the pH of the biocide solution and bleaching solution. Inorganic alkalinity donors are exemplified by: bicarbonate, carbonate, phosphate, borate, and silicate. Organic alkalinity donors include amines. Specific non-limiting examples include sodium bicarbonate, potassium bicarbonate, sodium carbonate, potassium carbonate, disodium phosphate, trisodium phosphate, sodium borate, sodium metasilicate, ethanolamine and the like.

As used herein, "reactive oxygen species" are any combination or variants of oxygen and oxygen radicals that are effective oxidizers. Specific non-limiting examples of reactive oxygen species include but are not limited to singlet oxygen, superoxide, and hydroxyl radicals.

As used herein, "biocide composition" refers to a composition comprising at least one organic acyl polyoxychlorine that kills or inhibits the growth of microorganism such as bacteria. The biocide compositions inactivate microbiological organisms and are applied where antimicrobial activity is desired. Biocide compositions can be formulated with other additives and adjuvants to meet the requirements of specific applications, such as those requiring a disinfectant, sanitizer, and/or sporicide.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "disinfectant" refers to an agent that kills all vegetative cells including most recognized pathogenic microorganisms, using the procedure described in A.O.A.C. Use Dilution Methods, Official Methods of Analysis of the Association of Official Analytical Chemists, paragraph 955.14 and applicable sections, 15th Edition, 1990 (EPA Guideline 91-2).

As used in this invention, the term "sporicide" refers to a physical or chemical agent or process having the ability to cause greater than a 90% reduction (1-log order reduction) in the population of spores of Bacillus cereus or Bacillus subtilis within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

As used herein, "weight percent" and "wt %" and the like are synonyms that refer to the concentration of a substance as the weight of that substance divided by the weight of the composition and multiplied by 100.

As used herein, the term "recirculating system" refers to any open or closed aqueous system that comprises a reservoir of water and a system of piping to transport the water, and wherein the water transported through the piping is eventually returned to the reservoir. Examples of recirculating systems include but are not limited to: cooling systems including cooling towers and cooling ponds; swimming pools; fountains; chilled water systems, and feature pools. Recirculating systems shall also include "once through systems" wherein the water is passed once across the heat exchangers then returned to a reservoir such as a pond, lake, river, or holding tank.

As used herein, the term "food product" or "food" refers to any food or beverage item that may be consumed by humans or mammals. Some non-limiting examples of a "food product" or "food" include the following: meat products including ready-to-eat ("RTE") meat and poultry products, processed meat and poultry products, cooked meat and poultry products, and raw meat and poultry products including beef, pork, and poultry products; fish products including cooked and raw fish, shrimp, and shellfish; produce including whole or cut fruits and vegetables and cooked or raw fruits and vegetables; pizzas; ready made breads and bread doughs; cheese, eggs, and egg-based products; and pre-made food items such as pre-made sandwiches. The present invention is particularly useful for meat and poultry products. Specific examples of meat products including RTE deli or luncheon meats like turkey, ham, roast beef, hot dogs, and sausages. Additionally, the present invention can be used on bacon and pre-made, pre-assembled, or pre-packaged meals such as TV dinners and microwaveable entrees or meals.

As used herein "food processing systems" refers to the surfaces of equipment and surroundings used to process food. Food processing systems includes the equipment and building structures used to process, produce, store, wash, move, sanitize, cut, and package consumable food items.

As used herein, "food intervention" refers to the treatment of a food product or food, and/or food processing systems with a biocide composition comprising an organic acyl polyoxychlorine to killing one or more of the food-borne pathogenic bacteria associated with a food product, such as *Salmonella typhimurium, Salmonella javiana, Campylobacter jejuni, Listeria monocytogenes, Escherichia coli* O157:H7, and the like.

As used herein, "hard surfaces" include: countertops; floors; walls; tables; cabinets; doors; doorknobs; food processing equipment, and the like. Hard surfaces are found in industrial and institutional facilities including hospitals, food processing facilities, day care centers, nursing homes, cafeterias, Universities, schools, and the like.

As used herein, the phrase "health care equipment" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, "cold water sterilant" is a biocide composition used to sterilize endoscopes and other surgically used instruments that are susceptible to damage from heat. Cold water sterilant may be effective at temperatures ranging, for example from 4° C. and above.

As used herein, "paper pulp" describes a slurry comprising water, lignin, and cellulose. Paper pulp, the raw material in paper, is not naturally white, its light color or pure whiteness is the result of a multi-phased bleaching process. Bleaching removes or alters the color substances in the paper pulp by oxidizing the lignin based chromophores.

As used herein, "bleach composition" comprises at least one organic acyl polyoxychlorine compound and a carrier. Bleach compositions of the invention are effective at oxidizing chromophores and oxidizable organics, thereby reducing or removing color and odor from laundry articles, paper pulp, and common hard-surface stains. Specific non-limiting examples of applications suitable for application of bleach compositions include: laundry, textiles, dishwashing, countertops, swimming pools, cooling towers, denture cleaning, carpet cleaning, paper pulp bleaching, decontamination of military equipment, and the like.

As used herein, "laundry" refers to fabric based clothing, uniforms, towels, rags, and linens that require cleaning to remove stain causing chromophores, dirt, undesirable dye, and/or sanitizing or disinfecting to remove pathogens.

As used herein, "laundry wash-water" refers to water or aqueous solution used to clean, bleach, sanitize and/or disinfect fabric based clothing, uniforms, towels, rags, and linens.

As used herein, "octanol/water partition coefficient" is the Log value of the concentration of the organic acyl polyoxychlorine compound measured in the octanol phase divided by the concentration of the organic acyl polyoxychlorine compound measured in the water phase. The reported value is reported as the Log P value. In general terms, a negative Log P value indicates that more of the organic acyl polyoxychlorine compound is measured in the water phase, while a positive Log P value indicates more of the organic acyl polyoxychlorine compound is measured in the octanol phase.

The Log P value of the biocide compositions takes into account the use of charge neutralizing cations, surfactants, carriers, and penetrators that enhance the distribution of the organic acyl polyoxychlorine compound into the octanol phase.

As used herein, "use-conditions" refers to the octanol/water partition coefficient of the organic acyl polyoxychlorine under the conditions in which it is being applied. For example, application of a biocide composition of the invention to a cooling tower recirculating system treated with an alkaline pH treatment will require the organic acyl polyoxychlorine to perform its antimicrobial function at a pH of 8.0 to 9.5. Under these conditions, the antimicrobial efficacy of hydrophilic organic acyl polyoxychlorine compounds would be compromised unless the biocide composition is formulated with carriers or penetrations to increase the lipophilicity of the organic acyl polyoxychlorine. However, organic acyl polyoxychlorine compounds comprising a primary carbon based structure that provides a high level of hydrophobicity and lipophilicity under these pH conditions may be used along or in combination with carriers and penetrators that increase lipophilicity.

It is therefore desirable and advantageous to assess the Log P value of the octanol/water partition coefficient under the condition in which the biocide composition is being employed. Preferably an octanol/water partition coefficient under use-conditions is at least 0.5, more preferably, at least 1.0, and most preferably at least 1.5.

As used herein, "charge neutralizing cations" neutralize the anionic charge of the organic acyl polyoxychlorine, thereby increasing the octanol/water partition coefficient and lipophilicity. Specific non-limiting examples of charge neutralizing cations include: hydronium ions ($H_3O^+$), ammonium ions ($NH_4^+$), primary amines, secondary amines, tertiary amines, quaternary amines, biquanides, and may include zwitterion surfactants.

DETAILED DESCRIPTION OF THE INVENTION

It has been discovered that stable organic acyl polyoxychlorine compositions can be produced that are extremely effective biocide compositions and bleach compositions. These compositions provide unprecedented features and benefits compared to other oxidizing bleaches and antimicrobials exemplified by sodium hypochlorite, hydrogen peroxide, chlorine dioxide, peroxyacids, and non-oxidizing biocide exemplified by quaternary ammonium chloride, biquanide and the like.

Without being bound by a particular theory, it is believed that the improved efficacy of the biocide and bleach compositions of the invention is the result of the functionality of the acyl polyoxychlorine group and the subsequent series of intermediates produced during the cascading reduction of the oxychlorine intermediate (the leaving group).

The organic acyl polyoxychlorine compounds of the invention having the general formula:

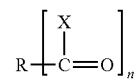

wherein (X) comprises a polyoxychlorine selected from at least one of a chlorate having the general formula $ClO_3$ and perchlorate having the general formula $ClO_4$;

(R) comprises hydrogen or a $C_1$ to $C_{23}$ primary carbon based structure; and where (n) is one or more acyl polyoxychlorine groups.

Functionality—Trigger

Without being bound by a specific theory, it is believed that the functionality of the acyl polyoxychlorine group is that of a trigger. When the trigger is actuated by chemical reduction, the acyl polyoxychlorine group releases a reactive oxychlorine intermediate.

When a polyoxychlorine anion is reacted with the organic acyl group as a result of nucleophilic substitution at the acyl carbon (exemplified by chlorate anion reacted with an acyl group provided by carboxylic acid or carboxylic acid derivatives) it forms a chemical structure having the general formula

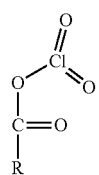

The single bonded oxygen attached to the chlorine of the chlorate anion, reacts with the carbon atom comprising the acyl group as a result of nucleophilic substitution of the acyl carbon. The "functionality of the acyl polyoxychlorine" comes from the formation of a trigger that comprising the single bonded oxygen-chlorine bond.

When a source of available electrons (i.e. reducing agent) interacts and actuates the trigger, the oxygen-chlorine bond is cleaved, resulting in the formation of a carboxyl group, and release of a reactive oxychlorine intermediate that undergoes a series of cascading chemical reduction (reduction) reactions.

Surprisingly, the released oxychlorine intermediate results in the formation of chlorine dioxide, chlorite, and terminates with oxygen and chloride. The oxygen species produced during reduction of the oxychlorine intermediate mirror those resulting from reduction of peracetic acid. However the reduction of the oxychlorine intermediate results in a broader range of oxygen intermediates and higher magnitude peaks indicting higher concentrations (more oxygen released from the oxychlorine). The kinetic data illustrates the oxychlorine intermediate reduction goes to completion under the conditions it was tested, resulting in oxygen and a chloride salt. Once the reduction process is actuated, as long as an available source of electrons is present, the released intermediate undergoes cascading reduction until the decomposition of the oxychlorine intermediate is complete.

The organic acyl polyoxychlorine compounds can be viewed as a form of "sequestered chlorine dioxide". The organic acyl polyoxychlorine compounds are stabilized forms of chlorine dioxide that result in the release or formation of chlorine dioxide as one of the oxychlorine intermediates when the said oxygen-chlorine trigger is actuated.

Bond Realignment and Rearrangement

It has been demonstrated using UV spectral analysis under kinetic conditions that the oxychlorine intermediates undergo rapid and complete decomposition to benign termination products. Without being bound by a particular theory, it is theorized the alignment of the oxygen-chlorine bonds of the chlorate (or perchlorate) is influenced by the organic acyl donor. When the trigger of the organic acyl polyoxychlorine is actuated, the oxychlorine intermediate is released. The bond lengths and bond angles of the oxygen comprising the oxychlorine intermediate must shift to compensate for the loss of the organic acyl donor. The destabilized oxychlorine intermediate attempts to regain stability by drawing electrons from neighboring sources, inducing the need for another round of realignment. The resulting effect is a series of cascading reduction reactions resulting in decomposition of the oxychlorine intermediate that terminates with the formation of a chloride and oxygen.

Primary Carbon Based Structure (R)

The high level of survivability and stability in the presence of organic loading and over a wide range of pH conditions (such as a pH of 1 to 10) gives organic acyl polyoxychlorine compounds unprecedented versatility in formulating and use in application.

For example, in applications where hydrophilic bleaches are required, the (R) group may comprise hydrogen or $C_1$ to $C_7$ primary carbon based structures. Simple and inexpensive short chain fatty acids, dicarboxylic acids, and cyclic anhydrides can also be used as desired to produce the organic acyl polyoxychlorine compounds for this application.

In biocide compositions where penetrators are utilized to enhance the permeation into the membranes of microbes, a broad range of primary carbon based structures can be used. For example $C_1$ to $C_{17}$ primary carbon based structures may be employed. In this example, inexpensive short chain and medium chain fatty acids can be used to produce the organic acyl polyoxychlorine, commercially available carboxylic acid based surfactants, and the like can be used to produce the organic acyl polyoxychlorine.

In biocide applications where the primary carbon based structure requires wetting, surface activity, and membrane permeation, generally $C_7$ to $C_{17}$ primary carbon based structures are employed. Again, low cost products can be produced using saturated and unsaturated alkyl fatty acids to produce the organic acyl polyoxychlorine.

Further still, in combined applications such as in the case of laundry bleaching wherein antimicrobial activity is desired, and/or both hydrophilic and hydrophobic based stain removal is desired, the primary carbon based structure may incorporate a broad range of structures from $C_1$ to $C_{23}$, more preferred $C_3$ to $C_{17}$, and most preferred $C_7$ to $C_{13}$. For these types of applications, manufactured and commercially available surfactants exemplified by: alkylimidazoline propionate, cocaminopropionic acid, octyliminodipropionic acid, and laureth sulfosuccinate may be converted into organic acyl polyoxychlorine compounds. While more expensive, they provide surfactant properties required in the wash water as well as a dual role of a bleaching agent that can target hydrophobic stains, which are often considered the more difficult types of stains to remove.

In bleaching applications, the ability to utilizing hydrophilic and hydrophobic organic acyl polyoxychlorine compounds allows for the targeting and delivery of the "sequestered chlorine dioxide" to the stain causing chromophores it is best suited to oxidize. Hydrophilic properties enhance decomposition of water soluble chromophores while hydrophobic properties enhance adsorption to hydrophobic chromophores.

When interaction occurs between the activated organic acyl polyoxychlorine and chromophore, the trigger is actuated and the reactive oxychlorine intermediate is released at the site of the stain. When addressing hydrophobic chromophores, primary carbon based structures that improve wetting (i.e. $C_7$ to $C_{11}$), as well as commercially available surfactant based organic acyl polyoxychlorine compounds improve wetting to penetrate hydrophobic deposits, adsorption onto hydrophobic stains, and surfactant properties that enhance dispersion of chromophore fragments. They can also provide a dual role of sanitizing and/or disinfecting.

For these reasons, the primary carbon based structure (R) comprises a wide range of structures and moiety to allow for the unique features and benefits provided by the organic acyl polyoxychlorine compounds so that may be produced and utilized to obtain maximum efficacy in a broad range of antimicrobial, bleaching, and cleaning applications.

Structures

The primary carbon based structure (R) comprises an: alkyl, arylalkyl, cycloalkyl, aromatic, or heterocyclic group.

The primary carbon based structure (R) can be saturated or unsaturated as well as substituted or unsubstituted.

The primary carbon based structure (R) may be substituted with moiety exemplified by: amino, amide, sulfonate, carboxylate, alkoxylate, hydroxyl, carbonyl, and phosphonate.

For antimicrobial applications and bleaching hydrophobic based stains, of particular interest and benefit are primary carbon based structure (R) that gives the organic acyl polyoxychlorine compound an octanol/water partition coefficient (Log P) of at least 0.5, more preferably greater than 1.0, and most preferably greater than 1.5.

Furthermore, a primary carbon based structure (R) that makes the organic acyl polyoxychlorine compound surface active and assist in wetting hydrophobic surfaces is preferred.

In one embodiment the primary carbon based structures (R) include $C_7$ to $C_{11}$ alkyl groups that result in the formation of terminating carboxylic acid comprising: octanoic acid, nonanoic acid, decanoic acid, undecanoic acid, and dodecanoic acid.

Octanol/Water Partition Coefficient

The octanol/water partition coefficient is a ratio of concentrations of organic acyl polyoxychlorine compound between the two solutions. The logarithm of the ratio of the concentrations of the solute in the solvents is called log P. The log P value is also indicates the relative lipophilicity.

It is theorized the octanol/water partition coefficient of the biocide composition comprising an organic acyl polyoxychlorine compound affects the permeation rate through the cell membrane. An octanol/water partition coefficient that favors the hydrophilic phase reduces the penetration of the cell membrane and subsequently reduces the inactivation rate. However, an octanol/water partition coefficient favoring the hydrophobic phase increases penetration of the lipid layer of the cell membranes thereby increasing intracellular concentration and subsequent increased inactivation rates.

To further elaborate, membrane disruption is thought to be the primary mechanism of traditional oxidizing biocides. Peracetic acid and hypochlorite bleach are examples where the interaction with the cell membrane induces lysis. When organic acyl polyoxychlorine compositions interact with microbiological organisms, there does not appear to be the same interaction with cell membranes when the interactions occur externally at the cell membranes. If cell lysis resulted from oxidation of the lipid layer comprising the cell's outer membrane, the organic acyl polyoxychlorine would have comparable results to other oxidizing biocides when placed in contact with the cell membrane. However, the experimental data disclosed herein demonstrates otherwise.

In the following discussion, all referenced examples where test performed to determine the Rate of Kill of *S. aureus*.

In one illustrated example (Table 1), a composition comprising glycolyl chloride was compared to furoyl chlorate under acid conditions. Both the glycoyl chlorate and furoyl chlorate had equivalent moiety as it pertains to functionality (i.e. $ClO_3$). It would be expected that if the organic acyl polyoxychlorine functions like other oxidizing biocides, the inactivation rates would be comparable. Surprisingly, the results demonstrated a substantial difference in rate of kill.

The data indicates the carbon based structure of the (R) group can significantly influence the efficacy. For example, experimental data demonstrates lower biocide efficacy when the organic acyl polyoxychlorine comprises glycolyl chlorate as compared to furoyl chlorate. Glycolic acid has a reported Log P of less than −1.0, whereas furoic acid has a reported Log P of about 0.6.

However, when glycolyl chlorate is combined with a mixture of surfactants including nonionic and anionic surfactants exemplified by Tergitol TMN 3, Tergitol TMN 6, and Dowfax C10L, the rate of kill was increased by 5-log.

The compelling difference is the octanol/water partition coefficient (Log P) of the two biocide compositions and the ability of the organic acyl polyoxychlorine ability to permeate the lipid layer of the cell membrane.

Of most significance is the octanol/water partition coefficient under the conditions in which the biocide composition is being applied. For example, as the pH increases the anionic charge on the organic acyl polyoxychlorine has greater influence, and the organic acyl polyoxychlorine becomes more hydrophilic as the pH approaches and exceeds its pKa value.

Therefore, the octanol/water partition coefficient (Log P) of most importance is that of the organic acyl polyoxychlorine compound under the conditions in which it is applied to (or contacted with) the microbiological organisms. For example, a biocide composition which comprises a primary carbon based structure, surfactant, carrier, penetrator, and/or charge neutralizing cations that increase the lipophilicity of the organic acyl polyoxychlorine compound will provide higher antimicrobial efficacy due to increased permeation of the cell membranes of the microbiological organisms.

In another illustrated example (Table 2), organic acyl polyoxychlorine compounds comprising primary carbon based structures that increase the octanol/water partition provide higher rate of kill at higher pH. For example, furoyl chlorate was compared to benzoyl chlorate and octanoyl chlorate at comparable pH of 5.5 to 6.5. In previous examples, furoyl chlorate under acid pH conditions provided excellent rate of kill. However, as pH is increased, and the furoyl chlorate becomes unprotonated, the rate of kill decreases until it demonstrates no antimicrobial efficacy at about pH 7. Benzoyl chlorate demonstrates similar behavior. Under acid pH conditions, benzoyl chlorate demonstrates excellent rate of kill. However at pH of about 7, without use of penetrators and the like, benzoyl chlorate demonstrates no recognizable biocide efficacy. However, octanoyl chlorate, even at a pH approaching 6 demonstrates excellent rate of kill.

Based on the experimental evidence and without being bound by any theory, the organic acyl polyoxychlorines of the invention appear to perform their function as a biocide by intracellular action. In this manner, the organic acyl polyoxychlorine compounds of the invention demonstrate behavior comparable to that of a drug more so than that of a traditional prior art oxidizing biocide. This unique feature provides significant benefits as it pertains to formulating stable biocide compositions and applications wherein high organic loading and elevated pH would otherwise compromise the efficacy of other oxidizing biocide.

It is preferred the biocide composition provide an octanol/water partition coefficient of the organic acyl polyoxychlorine compound under "use-conditions" be preferably greater than or equal to 0.5, more preferably greater than or equal to 1.0, and most preferably greater than or equal to 1.5.

In chemistry and the pharmaceutical sciences, a partition coefficient (P) or distribution coefficient (D) is the ratio of concentrations of a compound in the two phases of a mixture of two immiscible solvents at equilibrium. While reference to different coefficients may be made, the objective as it pertains to the ability to permeate the membranes of a microbiological organism, or affinity to a hydrophobic substance is deemed comparable to the octanol/water partition coefficient with respect to reference to the invention.

Increasing Lipophilicity

When the polyoxychlorine anion is reacted with the organic acyl donor, the resulting organic acyl polyoxychlorine compound possesses a strong anionic charge. Without being bound by any theory, it is believed the strong polar charges reduce the lipophilicity of the said compound and its subsequent biocidal efficacy.

This theory is consistent with results obtained by test performed at various pH using various organic structures. At low pH where there is an excess of hydronium ions and the anionic charges are neutralized due to protonation, the biocide efficacy of organic polyoxychlorine compounds having lower carbon based structures is increased. As the pH is increased, the concentration of hydronium ions is reduced resulting in increased ionization of the organic acyl polyoxychlorine compound, and subsequent reduction in hydrophobicity, lipophilicity and cell membrane permeation. Furthermore, addition of penetrators exemplified by nonionic surfactants with low HLB values exemplified by Tergitol TMN 3 increased permeation and enhanced the rate of kill of the microorganisms of otherwise hydrophilic compounds. Further still, using (R) groups with higher octanol/water partition coefficient exemplified by $C_7$-$C_{11}$ primary carbon based structures further increased the Rate of Kill of *Staphylococcus aureus* even at pH values that resulted in negligible or no measurable antimicrobial efficacy from organic acyl polyoxychlorine compounds having lower carbon structures.

One possible method of enhancing the lipophilicity of the organic acyl polyoxychlorine compounds may be the addition of charge neutralizing cations. Non-limiting examples of charge neutralizing cations include but may not be limited to: hydronium; ammonium; amines including primary, secondary, tertiary, and quaternary; biquanides; and zwitterionic surfactants.

The use of certain charge neutralizing cations exemplified by ammonium ions allows the use of formulations with higher pH values than in the case when hydronium ions are used. Compositions with near neutral pH can be formulated while demonstrating excellent cell permeability due to the charge neutralizing effect provided by the cations.

Penetrators exemplified by Capmul products are mono- and diglyceride emulsifiers prepared through the glycerolysis of select fats and oils. Penetrators increase the lipophilicity of drugs to enhance their permeation thru cell membranes.

Stabilized and Activated Organic Acyl Polyoxychlorine Compounds

The organic acyl polyoxychlorine compounds of the invention have been shown to be extremely stable under a wide range of pH, and in the presence of a wide range of organic compounds that can be used in combination with the organic acyl polyoxychlorine to further enhance performance.

The stability of the organic acyl polyoxychlorine also increases its utility in applications where high organic load maybe present such as in the case of food intervention, contaminated surgical equipment, and contaminated cooling water used to cool heat exchangers in refineries and other industries where organic based contamination is common.

It has been discovered the stability of the organic acyl polyoxychlorine can be used to its advantage by reducing the indiscriminate decomposition of the organic acyl polyoxychlorine. By properly selecting pH buffering agents, the stabilized organic acyl polyoxychlorine can be applied to many applications efficiently for microbial control where other, more reactive biocides would undergo reduction resulting from the high oxidant demand.

However, it has been discovered the stability of the organic acyl polyoxychlorine can be compromised by buffering an acid pH solution of organic acyl polyoxychlorine with a carbon dioxide based alkalinity exemplified by sodium bicarbonate. This method of destabilization can also be performed in reverse by acidifying an alkaline pH solution of organic acyl polyoxychlorine buffered with bicarbonate or carbonate based alkalinity. The destabilizing action of the organic acyl polyoxychlorine is best achieved when the pH is buffered to 5.0 to 7.0. Excessive buffering that results in a pH that does not allow release of carbon dioxide, or allow decomposition of carbonic acid, may stabilize at least some portion of the organic acyl polyoxychlorine.

Without be bound to by a particular theory, it is thought that the pH buffering resulting from use of carbonate based alkalinity in the presence of acid releases carbon dioxide, which in turn results in an imbalance in counter ions in the solution. The loss of the counter ions imposes a destabilizing effect on the organic acyl polyoxychlorine so that the functional trigger previously described is readily actuated in the presence of many organics such as chromophores. When other pH buffering agents are used, such as phosphates, borates, silicates, and amines, the organic acyl polyoxychlorine is substantially stable and can be stored and/or formulated with many types of organics such as germinates and surfactants to enhance biocide performance.

However, destabilization of the organic acyl polyoxychlorine compounds by pH neutralization with carbon dioxide based alkalinity allows for a near neutral bleaching with a high level of efficacy while being color safe and reducing potential of damage to fabrics.

Preferred Embodiments

In one embodiment of the invention, there is provided biocide and/or bleach compositions comprising an organic acyl polyoxychlorine compound having the general formula:

wherein (X) comprises a polyoxychlorine selected from at least one of a chlorate having the general formula $ClO_3$ and perchlorate having the general formula $ClO_4$;

(R) comprises hydrogen or a $C_1$ to $C_{23}$ primary carbon based structure;

where (n) is one or more acyl polyoxychlorine groups;

wherein chemical reduction of the organic acyl polyoxychlorine results in formation of oxychlorine intermediates; and where at least one of the oxychlorine intermediates is chlorine dioxide.

In certain embodiments, the primary carbon based structure (R) comprises an: alkyl, arylalkyl, cycloalkyl, aromatic, or heterocyclic group. The primary carbon based structure can be saturated or unsaturated as well as substituted or unsubstituted.

In certain embodiments, the primary carbon based structure (R) may be substituted with moiety exemplified by:

amino, amide, sulfonate, carboxylate, alkoxylate, alkyl, hydroxyl, carbonyl, and phosphonate.

In certain embodiments, the primary carbon based structure (R) comprises a saturated or unsaturated $C_1$ to $C_{17}$ alkyl group.

In certain embodiments, the primary carbon based structure (R) comprises a saturated or unsaturated $C_3$ to $C_{17}$ alkyl group.

In certain embodiments, the primary carbon based structure (R) comprises $C_4$ to $C_5$ heterocyclic group.

In certain embodiments, the primary carbon based structure (R) gives the organic acyl polyoxychlorine compound an octanol/water partition coefficient (Log P) of at least 0.5, more preferably greater than 1.0, and most preferably greater than 1.5.

In certain embodiments, the primary carbon based structure (R) selected makes the organic acyl polyoxychlorine compound surface active and assist in wetting hydrophobic surfaces.

In one embodiment of the invention, there is provided a biocide composition comprising at least one organic acyl polyoxychlorine and carrier.

In another preferred embodiment of the invention, there is provided a biocide composition comprising at least one organic acyl polyoxychlorine having the general formula:

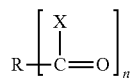

wherein (X) comprises a polyoxychlorine selected from at least one of a chlorate having the general formula $ClO_3$ and perchlorate having the general formula $ClO_4$;

(R) comprises hydrogen or a $C_1$ to $C_{13}$ primary carbon based structure;

where (n) is one or more acyl polyoxychlorine groups; and carrier.

In one embodiment of the invention, there is provided a method of killing microorganisms comprising contacting microbiological organisms with a biocide composition comprising an organic acyl polyoxychlorine and carrier.

In one embodiment of the invention, there is provided a bleach composition comprising at least one organic acyl polyoxychlorine and carrier.

In another preferred embodiment of the invention, there is provided a bleach composition comprising at least one the organic acyl polyoxychlorine having the general formula:

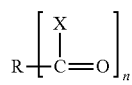

wherein (X) comprises a polyoxychlorine selected from at least one of a chlorate having the general formula $ClO_3$ and perchlorate having the general formula $ClO_4$;

(R) comprises hydrogen or a $C_1$ to $C_{23}$ primary carbon based structure;

where (n) is one or more acyl polyoxychlorine groups; and a carrier.

In another embodiment of the invention, a method of bleaching comprising contacting chromophores with a bleach composition comprising organic acyl polyoxychlorine and a carrier.

In one embodiment of the invention, a method of bleaching comprising contacting chromophores with a bleach composition comprising activated organic acyl polyoxychlorine.

Specific non-limiting examples of organic acyl polyoxychlorine comprising various primary carbon based structures include but are not limited to:

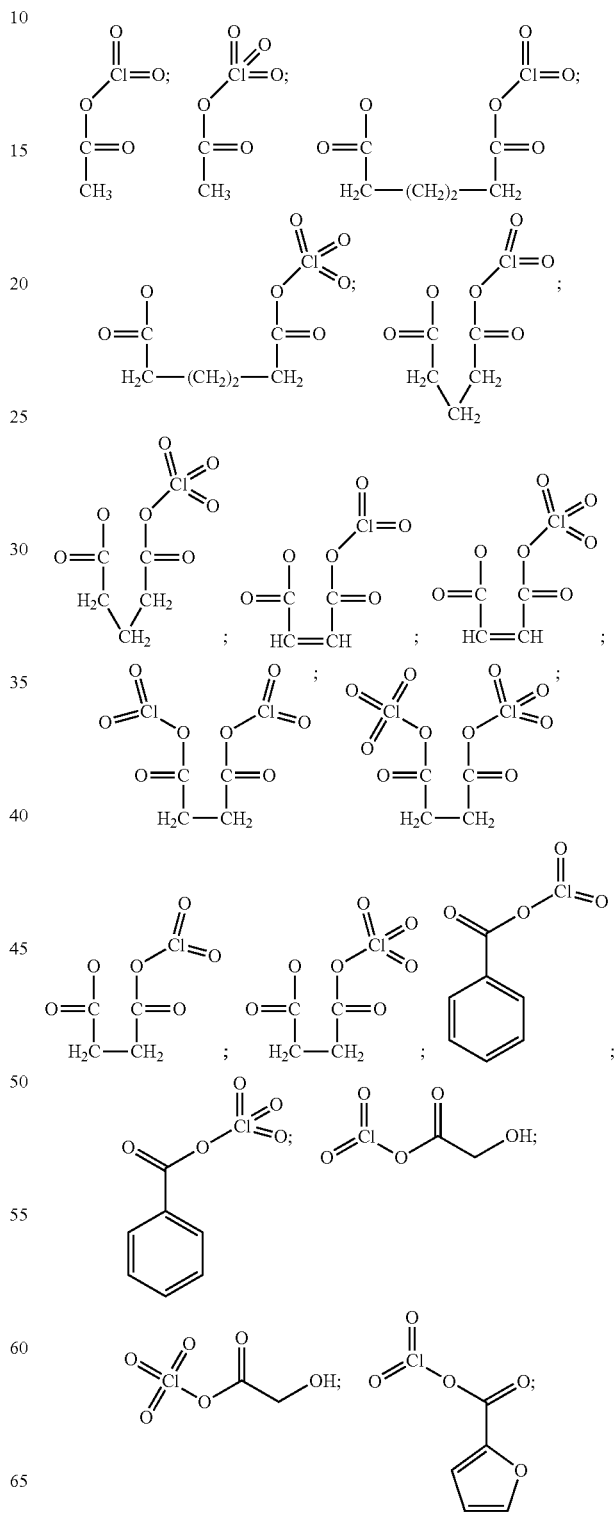

-continued

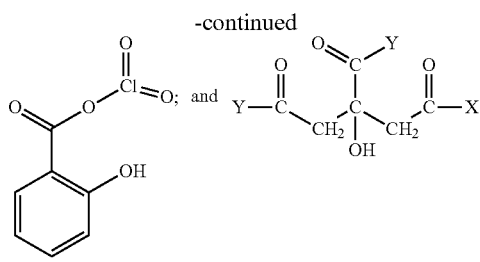

wherein "X" comprises at least one of a chlorate having the general formula $ClO_3$ and perchlorate having the general formula $ClO_4$; and "Y" comprises at least one of an oxygen, ester, chlorate having the general formula $ClO_3$, and perchlorate having the general formula $ClO_4$.

Preferred specific non-limiting examples of organic acyl polyoxychlorine compounds that provide increased hydrophobicity and are inexpensive to produce include but are not limited to:

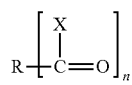

wherein (X) comprises a polyoxychlorine selected from at least one of a chlorate having the general formula $ClO_3$ and perchlorate having the general formula $ClO_4$;

(R) comprises saturated or unsaturated $C_7$ to $C_{17}$ alkyl group; and where (n) is one or more acyl polyoxychlorine groups.

Reactants for Producing Organic Acyl Polyoxychlorine

Organic acyl donors, for example, may include carboxylic acid and carboxylic acid derivatives exemplified by acyl chlorides (RCOCl), acid anhydrides ($RCO_2COR$), esters ($RCO_2R$), amides ($RCONH_2$), salts of carboxylic acids such as sodium, potassium, lithium, and ammonium.

Carboxylic Acids

Carboxylic acids are suitable as a source of organic acyl donors for the production of organic acyl polyoxychlorine. Examples of saturated alkyl carboxylic acid include but are not limited to: methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, icosanoic acid, 2-methylpropenoic acid, 2-butenoic acid, sorbic acid, caproic acid, 2-methylpentanoic acid, 2-ethylbutanoic acid, phenylethanoic acid, 2-methylbenzoic acid, 3-methylbenzoic acid, 4-methylbenzoic acid, benzoic acid, 2-ethylhexanoic acid, 2-propylpentanoic acid, 3-phenyl-2-propenoic acid, 2-phenylpropanoic acid, 3-phenylpropanoic acid, 3-methylphenylethanoic acid, 4-methylphenylethanoic acid, 2-propylhexanoic acid, 2-methyl-3-phenylpropenoic acid, 2-propylheptanoic acid, 2-butylhexanoic acid, 5-phenyl-2,4-pentadienoic acid, diphenylethanoic acid, anthracene-9-carboxylic acid, 8-hexadecenoic acid, 9,12,15-octadecatrienoic acid, 9,12-octadecadienoic acid, 9-octadecenoic acid, octadecanoic acid, 5,8,11,14-eicosatetraenoic acid, eicosanoic acid, and the like.

Fatty Acids

Fatty acids are inexpensive sources of organic acyl donors that can be selected to provide increased hydrophobicity to enhance bleaching of hydrophobic chromophores as well as result in formation of lipophilic organic acyl polyoxychlorine compounds for enhanced permeation of cell membranes.

Non-limiting examples of saturated alkyl fatty acids include but are not limited to: caprylic acid, capric acid, lauric acid, myristic acid, palmitic acid, stearic acid, arachidic acid, behenic acid, lignoceric acid.

Non-limiting examples of unsaturated alkyl carboxylic fatty acid include but are not limited to: myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid.

Acid anhydrides react with the polyoxychlorine anion when the composition is contacted with water to produce at least one of a biocide solution and bleach solution. Specific non-limiting examples of acid anhydrides include but are not be limited to succinic anhydride, maleic anhydride, N-caprylic anhydride, acetic anhydride, glutaric anhydride, dimethyl glutaric anhydride, (2-Dodecen-1-yl)succinic anhydride, (2-Nonen-1-yl)succinic anhydride, and benzoic anhydride.

The organic acyl donor may be selected to provide synergy exemplified by surfactancy, dispersion, sequestration, and chelation as well as intended oxidation provide by the reduction of the organic acyl polyoxychlorine. A broad range of organic acyl donors can be used to obtain a synergistic effect and/or expand the options for formulating to obtain the desired organic acyl polyoxychlorine.

Specific non-limiting examples of organic acyl donors include but are not be limited to: formic acid, glycolic acid, lactic acid, adipic acid, succinic acid, 2-furoic acid, citric acid, fumaric acid, acetic acid, acetic anhydride, tartaric acid, maleic acid, glutaric acid, adipic acid monoethyl ester, inositol hexanicotinate, nicotinamide, nicotinic acid, anthranilic acid, inositol benzoate, phosphonobutane tricarboxylic acid, polyexpoxysuccinic acid, carboxyl $C_{11}$ dimethyl phosphonic acid, carboxyl $C_{11}$ diethyl phosphonic acid, carboxyl $C_{11}$ phosphonic acid, carboxyl $C_6$ phosphonic acid, laureth sulfosuccinate, benzoic acid, phthalic acid, isomers of phthalic acid, salicylic acid, picolinic acid, pyridine-2,6-dicarboxylic acid, 2-thiophenecarboxylic acid, 2-furoic acid, acetyl chloride, acetic anhydride, succinic anhydride, benzoic anhydride, phthalimido-hexanoic-acid, cyclopentane carboxylic acid, pyrrole-2 carboxylic acid, octanoic acid, lauric acid, benzoic acid, carboxylated nonylphenol, alkylimidazoline propionate, cocaminopropionic acid, octyliminodipropionic acid, and the like.

Polyoxychlorine anion donors useful in the practice of the invention include but are not limited to alkali metal salts, alkali earth salts, ammonium salts of chlorate and perchlorate. Acid forms of chlorate (chloric acid) and perchlorate (perchloric acid) are also suitable polyoxychlorine anion donors. Specific non-limiting examples of polyoxychlorine anion donors include lithium chlorate, sodium chlorate, potassium chlorate, magnesium chlorate, calcium chlorate, ammonium chlorate, chloric acid, lithium perchlorate, sodium perchlorate, potassium perchlorate, magnesium perchlorate, calcium perchlorate, ammonium perchlorate, perchloric acid.

Methods of Preparing Organic Acyl Polyoxychlorine

The following description and methods for producing the organic acyl polyoxychlorine compounds of the invention are non-limiting examples. The benefits of the invention over the prior art are the result of the functionality, properties, and/or characteristics provided by the organic acyl polyoxychlorine and are not limited by the methods, chemistries or techniques for production of the organic acyl polyoxychlorine.

Introduction:

During the formation of organic acyl polyoxychlorine compounds, it is preferred the organic acyl polyoxychlorine be produced absent of other compounds that may impede the production (competing reactions), decompose the organic acyl polyoxychlorine during production or storage (reducing agents), or form undesirable oxidation byproducts and intermediates such as alkyl chlorates and alkyl perchlorates.

Alkyl perchlorates exemplified by methyl perchlorate and ethyl perchlorate are alkylating agents that would make the biocide and bleach compositions undesirable due to likely health hazards resulting from direct and indirect contact with mammals and food products. For example, direct contact of alkylating agents with skin is known to induce ulcerations, and tumors.

In contrast to alkyl perchlorates, when the organic acyl polyoxychlorine compositions of the invention are reduced, they form carboxylic acids, and release an intermediate that is readily reduced to termination products that are Generally Recognized As Safe.

It is therefore desirable to produce the organic acyl polyoxychlorine compounds under conditions that favor nucleophilic substitution of the acyl carbon, and/or provide and excess of organic acyl donors in molar relation to the polyoxychlorine anion donors.

Discussion:

The reactants capable of producing the organic acyl polyoxychlorine compounds include carboxylic acids and derivatives of carboxylic acids. The conditions necessary to produce the desired organic acyl polyoxychlorine can vary significantly dependent on the source of organic acyl donor. For example, acyl chlorides are very susceptible to nucleophilic acyl substitution when mixed with polyoxychlorine anion donors. Acid anhydrides are also very useful and are readily available in both solid and liquid forms. These readily reactive carboxylic acid derivatives allow for broader range of reaction conditions while resulting in efficient conversion of reactants to the desired organic acyl polyoxychlorine compounds.

Carboxylic acids, esters and amides may also be used to produce the organic acyl polyoxychlorine compositions of the invention but in general require their own set of conditions and/or longer reaction times when compared to acid anhydrides.

TAED (Tetra Acetyl Ethylene Diamine) is an amide containing carboxylic acid derivative that can be used with chlorate ($ClO_3$) and perchlorate ($ClO_4$) to produce organic acyl polyoxychlorine under alkaline conditions.

Examples of esters that may be suitable for producing organic acyl polyoxychlorine compounds in-situ or ex-situ include, but are not limited to: nonanoyloxybenzene sulfonate, lauroyloxybenzene sulfonate, decanoyloxybenzoic acid, acetylsalicylic acid and the like.

Auto-oxidation of aldehydes generates acyl radicals that may be suitable for production of organic acyl polyoxychlorine compounds.

NON-LIMITING EXAMPLES

The invention will now be further explained with reference to the following non-limiting examples.

Example 1

Organic acyl donors comprising fatty acids are useful in biocide and bleach applications. Many of the more difficult stains to remove during bleaching and the ability to permeate lipid membranes of microbes requires organic acyl polyoxychlorine compounds that are hydrophobic and lipophilic. Medium chain fatty acids comprising $C_6$ to $C_{12}$ carbon chains and longer chain fatty acids comprising $C_{14}$ to $C_{24}$ are very useful in these applications and are low cost to purchase. However, solubility limitations of the acids reduce the concentrations that can be used during the production, and final formulating of bleach and biocide compositions.

A technique was developed that has proven very useful in processing medium chain and long chain fatty acids into organic polyoxychlorine compounds.

Organic polyoxychlorine compounds comprising medium chain fatty acids and long chain fatty acids can be produced from fatty acids in relatively high concentrations utilizing the following non-limiting example.

90 ml of distilled water was placed into a 250 ml flask with a 1 inch magnetic stirrer. The flask was placed on top of a heated magnetic stirrer and the stirrer was turn on to form a small vortex. 6 ml of acrylic acid was added to the flask, followed by $NH_4OH$ addition until the pH was measured at to be between 6.0-6.5 (2 ml of stock $NH_4OH$ required). The temperature was monitored and sustained between 45-50° C. 4.0 grams of $NaClO_3$ was added to the flask while mixing. The viscosity of the mixture gradually reduced after the addition of the sodium chlorate. This observation was visible due to the increase in vortex depth which required a reduction in mixing speed. The mixtures color and clarity changed over time. The white opaque suspension transitioned to a hazy translucent solution. The reaction was allowed to continue for 3 hours.

A 2 ml sample was added to 6 ml of distilled water in a 25 ml vial. A stock HCl solution was added drop wise while swirling with periodic measure of the pH. The pH was reduced to 2.0-2.5. A 2 ml sample of saturated $NaHCO_3$ solution was added while swirling to liberate the carbon dioxide. The pH was approximately 6.5. A small scoop of whey protein was added and swirled in the solution causing a rapid decomposition of the whey protein and formation of rapidly ascending gas.

Example 2

Many acid anhydrides have slight to limited solubility in water. They slowly hydrolyze to their parent acid. When succinic anhydride is added in a granular/flake form to water that has been treated with sodium chlorate, the tendency is to either coalesce and sink to the bottom, or entrap gas and float. Since the chlorate anions must collide with the acid anhydride to convert the succinic anhydride to the desired succinyl chlorate, large clumps of succinic anhydride reduce the efficiency of conversion and subsequent yield of the succinyl chlorate. In this case, extended time will be required to convert the succinic acid produced by the hydrolysis of the succinic anhydride. One way to improve the dispersion of a solid form of acid anhydride is to reduce the particle size of the acid anhydride and combine the acid anhydride with a surfactant.

A mixture was made by combining 5 grams of succinic anhydride with 0.5 ml of Pluronic 31R1 which is a block copolymer of polyethylene oxide and polypropylene oxide. The two were mixed, then 9.5 grams of sodium bicarbonate where added and mixed. The ingredients where added to a coffee grinder and ground to form a fine fluffy powder that was easily removed from the grinder.

100 ml of cold water (8° C.) was added to a flask and 1.5 grams of the mixture was combined with 0.50 grams of sodium chlorate then added to the flask. The solution was manually mixed for approximately 30 seconds and allowed to rest undisturbed. The solution was hazy and no settling of particulate was observed. After approximately 15 minutes the solution was clear, the pH was 6.28. The resulting solution comprises a biocide composition of succinyl chlorate.

To a 10 ml sample of the biocide composition a ceramic cylinder prepared using the protocol from AOAC 966.04 was added. The reaction upon addition of the cylinder was spontaneous. Vigorous gas evolution occurred and after 35 seconds the reaction appeared to be completed.

The test illustrated that combining solid acid anhydride with surfactant exemplified by Pluronic 31R1 and reducing the particle size resulted in a readily dispersible composition that did not require continuous mixing. This would be advantageous for producing powerful biocide composition and bleaching compositions from solid reagents where equipment for mixing is not available. For example, one non-limiting example is an expedient cold sterilant for sterilizing endoscopes in field hospitals for the military. A solid composition for producing the cold water sterilant could be made by adding the solids to a jar, shaking until the solution is effectively dispersed, and allowing the reactant sufficient time to form the biocide composition.

In this example, 20 grams of succinic anhydride was combined with 1.0 grams Pluronic F127 and ground in a coffee grinder to form a mixture. 1.0 gram of the mixture was combined with 1.0 grams sodium chlorate and 1.0 gram sodium bicarbonate and added to 100 ml of water and mixed. The solution was clear in approximately 3 minutes, the pH was 6.05. A 2.5 ml sample of biocide solution was combined with 7.5 ml of water and swirled. A scoop of whey protein was added and swirled. The sample demonstrated excellent decomposition of the whey protein.

These tests illustrate that combining a surfactant exemplified by the block copolymers sold under the trade name Pluronic® to the ground solid acid anhydride significantly improves the dispersion of the acid anhydride and results in effective conversion of the acid anhydride to the desired organic acyl polyoxychlorine. The formation of the organic acyl polyoxychlorine from dry reactants can be achieved using this technique with very limited mechanical mixing.

Methods of Preparing Biocide and Bleach Compositions

After the organic acyl polyoxychlorine compounds are produced, they can be diluted, the pH can be adjusted, they may be easily and safely formulated with other additives and adjuvants to produce the desired product for bleaching and/or biocide applications.

The biocide and bleach compositions may have a range of physical forms. For example, the biocide and bleach compositions may be a solid, liquid, structured or thickened liquid or gel, pellet, prill, or a powder.

Carriers

The compositions of the invention can also include a carrier. The carrier provides a medium which dissolves, suspends, or carries the other components of the composition. For example, the carrier can provide a medium for solubilization, suspension, or production of organic acyl polyoxychlorine. The carrier can also function to deliver and wet the antimicrobial composition of the invention on an object. To this end, the carrier can contain any component or components that can facilitate these functions. Generally, the carrier includes primarily water which can promote solubility and work as a medium for reaction. The carrier can include or be primarily an organic solvent, such as simple alkyl alcohols, e.g., ethanol, isopropanol, n-propanol, dimethyl sulfoxide (DMSO), acetone and the like. Polyols are also useful carriers, including glycerol, sorbitol, and the like. Suitable carriers include glycol ethers. Suitable glycol ethers include diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether (commercially available as DOWANOL EPH™ from Dow Chemical Co.), propylene glycol phenyl ether (commercially available as DOWANOL PPH™ from Dow Chemical Co.), and the like, or mixtures thereof.

Coupling Agents

The antimicrobial composition includes one or more coupling agents for maintaining the raw materials of the composition in solution. The coupling agent is preferably a GRAS or food additive raw material. Some non-limiting examples of suitable coupling agents include propylene glycol esters, glycerol esters, polyoxyethylene glycerol esters, polyglycerol esters, sorbitan esters, polyoxyethylene sorbitan esters, polyoxyethylene-polyoxypropylene polymers, sulfonates, dioctyl sodium succinate, stearoyl lactylate, and complex esters such as acetylated, lactylated, citrated, succinhylated, or diacetyl tartarated glycerides. The coupling agent is preferably a sorbitan ester such as polyoxyethylene (20) sorbitan monooleate, commercially available as Polysorbate 80, polyoxyethylene (20) sorbitan monostearate, commercially available as Polysorbate 60, and polyoxyethylene (20) sorbitan monolaurate, commercially available as Polysorbate 20.

Penetrators

A penetrator is a chemical compound that increases the lipophilicity of the organic acyl polyoxychlorine to enhance permeation thru cell membranes. Drugs often include a penetrator to enhance the permeation of a drug through the cell membrane. Penetrators generally have low HLB (Hydrophilic-Lipophilic Balance) values <10. A penetrator may be non-ionic surfactants that increase the lipophilicity, or emulsifiers exemplified by Capmul products which are mono- and diglyceride emulsifiers prepared through the glycerolysis of select fats and oils. Oleic acid, decanoate esters are examples of penetrators used to increase lipophilicity of drugs to transport them through cell membranes. Terpenoids include .alpha.-terpinene, cineole, citral, citronellal, citronellol, farnesol, geraniol, limonene, linalool, methone, nerolidol, terpineol, camphene, menthone, myrcene, nerol, tetrahydrogeraniol, tetrahydrolinalool, apritone, and bisabolol. Another means of determining lipophilicity is OHLB (organic hydrophilic-lipophilic balance) value.

Other Optional Components

Alkalinity donors consume hydrogen ions, thereby inducing an increase in the pH of the aqueous biocide composition and bleaching composition. Alkalinity donors maybe included during the generation of the biocide and bleach compositions or may be used to activate the acidified biocide and bleach compositions. Specific non-limiting examples include sodium bicarbonate, potassium bicarbonate, sodium carbonate, potassium carbonate, disodium phosphate, trisodium phosphate, sodium borate, sodium metasilicate and the like. An alkalinity donor may be provided by aqueous solutions being treated by the biocide composition or bleach composition. Organic amines exemplified by ethanol amine have demonstrated excellent stability and pH buffering capacity in acyl polyoxychlorine solutions.

Acid donors provide hydrogen ions resulting in the formation of hydronium ions. Hydronium ions protonate the anionic charge of organic acyl polyoxychlorine compounds thereby neutralinizing their anionic charge and increasing their lipophilicity. Hydronium ions also neutralize carbonate based alkalinity that destabilizes the acyl polyoxychlorine functional trigger, thereby increasing its bleaching efficacy.

Acid donors can be organic or inorganic. Non-limiting examples of acid donors include but are not limited to: hydrochloric acid, phosphoric acid, sulfuric acid, sodium bisulfate, formic acid, acetic acid, glycolic acid, chloroacetic acid, dichloroacetic acid, succinic acid, malic acid, tartaric acid, citric acid and the like.

Oxidizers can enhance the performance of the biocide and bleach solutions by providing a synergistic effect. Non-limiting examples of oxidizers include: chlorine dioxide, hydrogen peroxide, peroxide donors such as sodium percarbonate, peracids such as peracetic acid and peroctanoic acid, persulfates such as sodium persulfates, monopersulfates such as potassium monopersulfates, chlorine and/or bromine donors such as sodium hypochlorite, bromochloridimethyl hydantoin, dichloroisocyanurate and the like. Additionally, catalyzed oxidizer systems can be included. Catalyzed oxidizer systems may include but are not limited to: hydrogen peroxide and ionic and colloidal silver, iron and/or manganese with persulfate, cobalt and/or iron with monopersulfate. Other metal catalyst may be included depending on the oxidizer and desired effect. Other metal catalyst include but are not limited to copper, and ruthenium. An additive that results in the formation of chlorine dioxide is exemplified by sodium chlorite. In the presence of acid anhydrides, the sodium chlorite and other sources of chlorite are converted to chlorine dioxide. Hydrogen peroxide can be included during or after production of the organic acyl polyoxychlorine to produce at least some portion of percarboxylic acid.

Non-oxidizing biocides can be formulated with organic acyl polyoxychlorine biocide compositions of the invention due to the high level of stability and the synergistic effect that can be achieved by combining biocides. Non-limiting non-oxidizing biocides may be exemplified by quaternary ammonium chlorides, biquanides, thymol, carvacrol, Bronopol, and the like.

Germinates that induce germination of spores can be included with organic acyl polyoxychlorine biocide compositions. Specific non-limiting examples of germinates include: L-alanine, inosine, dodecylamine, calcium dipicolinate, ammonium chloride, sugars, electrolytes and the like.

Surfactants can be incorporated into the biocide and bleach compositions to reduce the surface tension, improve wetting, improve detergency, and provide foaming capability. Specific non-limiting examples include Poly(ethylene glycol)-block-poly(propylene glycol)-block-poly(ethylene glycol) copolymer surfactants sold under the trade name Pluronic® manufactured by BASF (e.g. Pluronic 31R1, Pluronic P103), alkyldiphenyloxide disulfonate exemplified by Dowfax C10L and Dowfax C6L sold by Dow Chemical, Tergitol TMN6, Tergitol TMN3, Triton DF12, also sold by Dow Chemical, ethoxylated alcohols sold under the trade name Tomadol® and alkoxylated surfactants sold under the tradename Nonidet™ both sold by Air Products, alkylglycosides exemplified by Triton BG-10, Triton CG-50, Triton CG-110 sold by Dow Chemical, block copolymers exemplified by Pluronic P103, Pluronic 31R1 sold by BASF. Surfactants can also be useful for pretreating solid acid anhydrides to improve their dispersion in the aqueous solution to prevent coalescing or the anhydride and separation by settling or floatation. Surfactants are useful as detergents as well as increasing wetting and penetration of membranes, and deposits.

Dispersants such as tripolyphosphate, hexametaphosphate, polyacrylic acid, can be useful in dispersing soils in sterilant and other applications in which the biocide and bleach compositions must penetrate deposits to effectively inactivate microorganisms.

Sequestrants are useful in both biocide compositions and bleach compositions of the invention to penetrate deposits and soils, dissolve and stabilize various metals. Specific non-limiting examples of phosphonate compounds that may be suitable in biocide and bleach compositions include but may not be limited to: 2-Aminoethylphosphonic acid, Dimethyl methylphosphonate, 1-Hydroxy Ethylidene-1,1-Diphosphonic Acid, Amino tris(methylene phosphonic acid), Ethylenediamine tetra(methylene phosphonic acid), Tetramethylenediamine tetra(methylene phosphonic acid), Hexamethylenediamine tetra(methylene phosphonic acid), Diethylenetriamine penta(methylene phosphonic acid), Phosphonobutane-tricarboxylic acid, N-(phosphonomethyl)iminodiacetic acid, 2-carboxyethyl phosphonic acid, 2-Hydroxyphosphonocarboxylic acid, Amino-tris-(methylenephosphonic acid).

Chelants are useful in both biocide compositions and bleach compositions of the invention to penetrate mineral deposits, dissolve and stabilize various metals. Specific non-limiting examples of chelants that may be suitable in biocide and bleach compositions include but may not be limited to: ethylenediamine tetraacetic acid, diethylene triamine pentaacetic acid, N-(hydroxyl ethyl)ethylenetriaminetriacetic acid, nitrilotriacetic acid.

Corrosion inhibitors are useful for inhibiting the corrosion of metals, glass and materials that may be subjected to high concentrations of the biocide compositions and bleach compositions of the invention. Specific non-limiting examples include: sodium nitrate, sodium molybdate, sorbic acid, polyphosphates, sodium silicates, sodium borate, tolytriazole, carboxybenzotriazole, sodium tolytriazole.

Alcohols are often incorporated into formulations as solvents to enhance penetration of deposits and soils as well as improve solubility of some additives such as surfactants. Specific non-limiting examples of alcohols include: aliphatic alcohol exemplified by isopropyl alcohol, methanol, ethanol; aromatic alcohol exemplified by benzyl alcohol can be useful in biocide compositions; and polyhydroxy alcohols exemplified by glycerol, ethylene glycol, and propylene glycol which can also function as humectants.

Viscosity modifiers and Gel forming agents exemplified by natural, semisynthetic and synthetic polymers may be used to increase the viscosity of the formulations comprising the organic acyl polyoxychlorine compounds. The polymer can be natural, such as a gum (e.g. Xanthun gum, alginates, carrageenan), semisynthetic such as a polysaccharides (i.e. microcrystalline cellulose, methylcellulose, hydroxyethylmethylcellulose, hydroxypropylmethylcellulose), or synthetic such as a poloxamers and carbomers.

Indicators can be added to biocide compositions to indicate the activity of the oxidizing biocide. Methylene blue and amaranth are two examples of indicators that may be suitable for use in these compositions.

Other ingredients that may be used in stabilized biocide and bleach compositions of the invention include fragrances, dyes, and flavors to provide a desirable esthetic value.

Application of the Biocide Composition

Food Intervention

The biocide composition may be applied to the food product prior to, after, or substantially simultaneously with the packaging of the food product. Alternatively, the composition may be applied to the food product without packaging.

The biocide composition includes an amount of organic acyl polyoxychlorine effective for killing one or more of the food-borne pathogenic bacteria associated with a food product, such as *Salmonella typhimurium, Salmonella javiana, Campylobacter jejuni, Listeria monocytogenes*, and *Escherichia coli* O157:H7 and the like.

The biocide composition may be applied to the food product in any desired manner. In some embodiments, the biocide composition may be applied directly to the food product in a number of ways including spraying, misting, rolling, and foaming the biocide composition directly onto the food product and the like, and immersing the food product in the biocide composition. The biocide composition may be applied in an injection such as in an injection solution, or the biocide composition may be applied as part of a marinade or tenderizer that is applied to the food product.

The biocide composition may be indirectly applied to the food product. The biocide composition may be applied to the packaging prior to inserting the food product into the packaging or prior to applying the packaging to the food product. The biocide composition then contacts the food product when the food product is packaged. As used herein, a "packaged food product" means a food product that has been placed in packaging but not yet sealed. The biocide composition may be applied to the packaging after the food product has been inserted into the packaging or after applying the packaging to the food product (e.g., the biocide composition may be squirted or otherwise introduced into the packaging after the food has been placed in the packaging but prior to sealing the packaging). The biocide composition may be applied to the food product substantially simultaneously with the packaging of the food product. Additionally, food packaging or food casing (e.g., hot dog or sausage casing) may be coated, treated, or impregnated with the biocide composition, and the biocide composition is applied to the food product when the food product is placed inside the packaging or casing.

The biocide compositions can also be used on foods and plant species to reduce surface microbial populations; used at manufacturing or processing sites handling such foods and plant species; or used to treat process waters around such sites. For example, the biocide compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The biocide compositions of the invention can be used to treat produce transport waters such as those found in flumes, pipe transports, cutters, slicers, blanchers, retort systems, washers, and the like. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. The biocide compositions may also be used to treat animal carcasses to reduce both pathogenic and non-pathogenic microbial levels.

The biocide composition is useful in the cleaning or sanitizing of containers, processing facilities, or equipment in the food service or food processing industries. The biocide compositions have particular value for use on food packaging materials and equipment, and especially for cold or hot aseptic packaging. Examples of process facilities in which the biocide composition of the invention can be employed include a milk line dairy, a continuous brewing system, food processing lines such as pumpable food systems and beverage lines, etc. Food service wares can be disinfected with the biocide composition of the invention. For example, the biocide compositions can also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g.; dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The biocide composition may also be employed by dipping food processing equipment into the use solution, soaking the equipment for a time sufficient to sanitize the equipment, and wiping or draining excess solution off the equipment, The biocide composition may be further employed by spraying or wiping food processing surfaces with the use solution, keeping the surfaces wet for a time sufficient to sanitize the surfaces, and removing excess solution by wiping, draining vertically, vacuuming, etc. The biocide composition may also be employed by dipping food processing equipment into the use solution, soaking the equipment for a time sufficient to sanitize the equipment, and wiping or draining excess solution off the equipment, The biocide composition may be further employed by spraying or wiping food processing surfaces with the use solution, keeping the surfaces wet for a time sufficient to sanitize the surfaces, and removing excess solution by wiping, draining vertically, vacuuming, etc.

Food processing surfaces, food products, food processing or transport waters, and the like can be treated with liquid, foam, gel, aerosol, gas, wax, solid, or powdered biocide compositions according to the invention, or solutions containing these compositions.

The present method and system provide for contacting a food product with a biocide composition employing any method or apparatus suitable for applying such a biocide composition. For example, the method and system of the invention can contact the food product with a spray of the biocide composition, by immersion in the biocide composition, by foam or gel treating with the biocide composition, or the like. Contact with a spray, a foam, a gel, or by immersion can be accomplished by a variety of methods known to those of skill in the art for applying antimicrobial agents to food. Contacting the food product can occur in any location in which the food product might be found, such as field, processing site or plant, vehicle, warehouse, store, restaurant, or home. These same methods can also be adapted to apply the stabilized compositions of the invention to other objects.

The present methods require a certain minimal contact time of the composition with food product for occurrence of significant antimicrobial effect. The contact time can vary with concentration of the use composition, method of applying the use composition, temperature of the use composition, amount of soil on the food product, number of microorganisms on the food product, type of antimicrobial agent, or the like. For example, the exposure time can be at least 5 to 15 seconds.

In an embodiment, the method for washing food product employs a pressure spray including the composition. During application of the spray solution on the food product, the surface of the food product can be moved with mechanical action, e.g., agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, for example, can also be heated to a temperature of 15 to 20° C., preferably 20 to 60° C. to increase efficacy. The spray stabilized composition can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One automatic spray application involves the use of a spray booth. The spray booth substantially confines the sprayed composition to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the stabilized compositions of the invention. These steam jets can be used in combination with cooling water to ensure that the treatment reaching the food product surface is at a desired temperature, such as less than 65° C., e.g., less than 60° C. The temperature of the spray on the food product is important to ensure that the food product is not substantially altered (cooked) by the temperature of the spray. The spray pattern can be virtually any useful spray pattern.

Immersing a food product in a liquid stabilized composition can be accomplished by any of a variety of methods known to those of skill in the art. For example, the food product can be placed into a tank or bath containing the stabilized composition. Alternatively, the food product can be transported or processed in a flume of the stabilized composition. The washing solution can be agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the stabilized composition can be rinsed, drained, or evaporated off the food product.

In another alternative embodiment of the present invention, the food product can be treated with a foaming version of the composition. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. Examples of use solution levels of the foaming agents is from 50 ppm to 2.0 wt-%. At time of use, compressed air can be injected into the mixture, then applied to the food product surface through a foam application device such as a tank foamer or an aspirated wall mounted foamer.

In another alternative embodiment of the present invention, the food product can be treated with a thickened or gelled version of the composition. In the thickened or gelled state the washing solution remains in contact with the food product surface for longer periods of time, thus increasing the antimicrobial efficacy. The thickened or gelled solution will also adhere to vertical surfaces. The composition or the washing solution can be thickened or gelled using existing technologies such as: xanthan gum, polymeric thickeners, cellulose thickeners, or the like.

The present surfactant peroxycarboxylic acid antimicrobial compositions can be used in the manufacture of beverage, food, and pharmaceutical materials including fruit juice, dairy products, malt beverages, soybean-based products, yogurts, baby foods, bottled water products, teas, cough medicines, drugs, and soft drinks. The materials can be used to sanitize, disinfect, act as a sporicide for, or sterilize bottles, pumps, lines, tanks and mixing equipment used in the manufacture of such beverages. Further, the surfactant peroxycarboxylic acid antimicrobial compositions can be used in aseptic, cold filling operations in which the interior of the food, beverage, or pharmaceutical container is sanitized or sterilized prior to filling. In such operations, a container can be contacted with the sanitizing surfactant peroxycarboxylic acid composition, typically using a spray, dipping, or filling device to intimately contact the inside of the container with the surfactant peroxycarboxylic acid composition, for sufficient period of time to reduce microorganism populations within the container. The container can then be emptied of the amount of sanitizer or sterilant used. After emptying, the container can be rinsed with potable water or sterilized water and again emptied. After rinsing, the container can be filled with the beverage, food, or pharmaceutical. The container can then be sealed, capped or closed and then packed for shipment for ultimate sale. The sealed container can be autoclaved or retorted for added microorganism kill.

Veterinary

Biocide compositions of the invention can be applied to agricultural or veterinary objects or surfaces include animal feeds, animal watering stations and enclosures, animal quarters, animal veterinarian clinics (e.g. surgical or treatment areas), animal surgical areas, and the like.

Personal Care

Due to the high stability of organic acyl polyoxychlorine, biocide compositions may be formulated into crèmes, paste, lotions, gels, and wash solutions for treatment of acne, tooth paste and mouthwash for inactivation of microbiological organisms that induce acne, tooth decay, and bad breathe. Hand and body wash compositions may also be effective antimicrobial compositions while being mild to skin due to their relative selectivity of the organic acyl polyoxychlorine.

Wound Care

Due to the high stability of organic acyl polyoxychlorine, and relative selectivity due to intracellular activation, organic acyl polyoxychlorine may be an excellent candidate for use in wound care. Wound wash solutions, crèmes, paste, gels, may be suitable for inclusion of organic acyl polyoxychlorine compounds of the invention. The biocide compositions of the invention may also be embedded into wound dressings applied to a wound.

Hard and/or Soft Surfaces

Biocide compositions of the present invention can be used as a concentrate or as a diluted solution. A biocide composition can be applied to or brought into contact with an object by any conventional method or apparatus for applying an antimicrobial or cleaning composition to an object. For example, the object can be wiped with, sprayed with, foamed on, and/or immersed in the composition, or a diluted use solution made from the composition. The composition can be sprayed, foamed, or wiped onto a surface; the composition can be caused to flow over the surface, or the surface can be dipped into the composition. Contacting can be manual or by machine.

The compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard surface medical or surgical instruments and devices; and hard-surface packaging. Such hard surfaces can be made from a variety of materials including, for example, ceramic, metal, glass, wood or hard plastic.

Recirculating Systems

Cooling systems exemplified by once-through and cooling tower based recirculating systems can be effectively treated with biocide compositions of the invention. Cooling systems are prone to formation of biofilms and experience corrosion of heat exchangers due to microbial activity. Furthermore, loss of heat transfer and efficiency occurs when films biofilms form.

Biocide compositions of the invention provide significant benefits over other oxidizing biocides exemplified by hypochlorite bleach, bromine, and chlorine dioxide. First, organic acyl polyoxychlorine compounds, due to their high stability are readily compatible with corrosion inhibitors and deposit control agents used to treat industrial and HVAC cooling systems. Furthermore, their stability at elevated pH and in the presence of organic contaminants provides improved efficiency in alkaline pH cooling water treatment programs used in refineries, paper mills, food processing, chemical processing industries and the like.

By selecting organic acyl polyoxychlorine compounds that provide good hydrophobicity and lipophilicity in alkaline pH conditions, and/or including penetrators and carriers that further increase the lipophilicity in alkaline pH conditions.

To best meet the application needs of alkaline pH cooling water treatment programs $C_7$ to $C_{17}$ saturated and unsaturated alkyl primary carbon based structures are desirable. Non-limiting examples of organic acyl polyoxychlorine compounds suitable for alkaline pH cooling water treatment programs may include: octanoyl chlorate, octanoyl perchlorate, nonanoyl chlorate, nonanoyl perchlorate, decanoyl chlorate, decanoyl perchlorate, undecanoyl chlorate, undecanoyl perchlorate, dodecanoyl chlorate, dodecanoyl perchlorate, tridecanoyl chlorate, tridecanoyl perchlorate, oleoyl chlorate, oleoyl perchlorate and the like.

Biocide compositions of the invention can be applied as a shock feed, intermittent feed, and/or continuous feed. Generally, shock feed and intermittent feed can be achieved using chemical metering pumps, educators, manual feed, and the like. Continuous feed is typically accomplished using a chemical metering pump.

Biocide compositions can be applied to the cooling tower basin, cooling tower cold well, or any convenient location is the circulating system exemplified by injection prior to critical heat exchangers.

Biocide compositions can be stored in pails, drums, totes, or bulk tanks. Diluted solutions can be made in day-tanks wherein the biocide composition is diluted with water in a temporary storage tank and metered into the cooling system.

Recreational water system exemplified by Swimming pools, Water-Parks, and Spas experience: algae blooms; biofilms in the circulation system comprising piping and filter system; and outbreaks of parasitic disease from *Cryptosporidium*. Organic acyl polyoxychlorine based biocide compositions may be used as antimicrobial treatments for the control or eradication of these problematic microorganisms.

Application of Bleach Compositions

Laundry

Commercial and residential laundry can be effectively treated using bleach and biocide compositions of the invention. The bleaching compositions of the invention provide for the ability to perform effective bleaching at near neutral to neutral pH (e.g. pH of 5.0-7.0). Near neutral to neutral pH cleaning of laundry articles is highly desirable because it reduced damage to linens, and is consider by the U.S. EPA as more environmentally favorable.

The following excerpts from the U.S. EPA document entitled "Considerations for Industrial and Institutional Laundry Partnership" illustrate the desire for new technologies and their benefits. The document states:

Neutral pH

Cleaning systems that can run under neutral or near-neutral pH conditions reduce potential human health and environmental concerns associated with pH altering compounds. Two additives used in many conventional systems—alkali breakers (which raise alkalinity at the beginning of the wash cycle) and low pH sours (which lower alkalinity at the end) care a potential hazard to laundry room workers and may contribute to chemical overuse and waste.

Straight-Chain Carbon Molecules

Formulations with straight or linear carbon (i.e., alkyl) chains might present less environmental concerns than compounds containing highly branched molecules. Linear alkyl chains biodegrade more rapidly than highly branched chains. EPA encourages the use of substitutes for highly branched alkyl chains or highly branched hydrophobic molecular components like branched alkyls and branched propoxy and butoxy groups."

Near neutral to neutral pH bleaching and cleaning is highly desirable, and the use of linear alkyl based bleaches is also deemed environmentally favorable.

A preferred method of treating laundry articles is to "activate" the organic acyl polyoxychlorine by contacting an acidified bleach composition with a solution of water buffered with a carbonate based alkalinity in a manner that induces decomposition of the carbonate alkalinity and subsequent release of carbon dioxide.

One non-limiting example is to buffer the laundry wash-water with a carbonate based source of alkalinity exemplified by sodium bicarbonate. For example, the acidified bleach composition is contacted with the buffered laundry wash-water to achieve a pH of 5.0 to 7.5, preferably 5.5 to 7.0. The reaction between hydronium ions and carbonate based alkalinity results in release of carbon dioxide and subsequent activation of the organic acyl polyoxychlorine based bleach. The activated bleach is extremely effective at reacting with chromophores comprising stains as well as dyes resulting in/from dye transfer.

Bleach and biocide compositions can be used in traditional alkaline laundry treatments by addition of bleach and biocide composition to the laundry wash-water, or by direct application of the bleach composition to the laundry articles prior to washing.

The activation method described can be performed in reverse as well. That is, a carbonate based buffer bleach composition can be acidified to activate the organic acyl polyoxychlorine. Various methods can be employed to achieve similar result.

Pretreatment of laundry articles to remove stains can be accomplished by applying bleach compositions directly to the stain prior to washing. Another option is to apply the bleach composition to the stain, then soaking the laundry article in a solution of water treated with a source of carbonate alkalinity. Yet another option is to first wet the laundry article with a solution of water treated with a source of carbonate based alkalinity, then apply the bleach composition. The laundry article can be soaked or added to a laundry washing machine.

Bleach and biocide compositions can be added to the laundry wash-water using any convenient means desirable. For residential or home washing, the bleach and/or biocide compositions may be added to the washing machine either manually or by adding to the automatic chemical dispensing system where bleaches and other treatments are added. The laundry articles can also be pretreated with the compositions of the invention.

Commercial and industrial laundry can be treated using any convenient means desirable. Manual addition, chemical metering using chemical pumps or educators can also be used.

The methods and means of applying the bleach compositions of the inventions are wide ranging and are only limited in that the bleach composition, either concentrated or diluted must contact the chromophores of the stains targeted for removal.

Bleach and biocide compositions used for laundry applications can be comprised from organic acyl polyoxychlorine compound having the general formula:

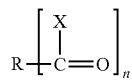

wherein (X) comprises a polyoxychlorine selected from at least one chlorate having the general formula $ClO_3$ and perchlorate having the general formula $ClO_4$;

(R) comprises hydrogen or a $C_1$ to $C_{23}$ primary carbon based structure; and where (n) is one or more acyl polyoxychlorine groups.

One particular embodiment is to produce organic acyl polyoxychlorine bleach and biocide compositions useful for laundry applications comprise $C_7$ to $C_{17}$ primary carbon based structures that result in termination carboxylic acids comprising saturated and/or unsaturated alkyl groups.

Generally, the (R) group comprising hydrogen or $C_1$ to $C_6$ primary carbon based structure are best suited for bleaching chromophores that favor the water phase (hydrophilic). Primary carbon based structure having $C_7$ to $C_{23}$ are more lipophilic and many (i.e. $C_7$ to $C_{13}$) provide surfactancy thereby increasing efficacy in bleaching hydrophobic favoring chromophores.

A cost effective bleach or biocide composition for laundry can be produced from fatty acids as well and commercially available carboxylic acids and carboxylic acid derivatives that provide terminating carboxylic acids having primary carbon based structures comprising saturated or unsaturated $C_7$ to $C_{17}$.

Testing

AOAC method 966.04 is used to determine the sporicidal efficacy of an antimicrobial agent. The test uses ceramic cylinders that have been placed in a suspension of proteinaceous materials and soils which had been inoculated with *Bacillus subtilis* and *C. Sporogenes*. The coated cylinders are removed from the suspension and dried. This preparation embeds the spores in a heavily soiled proteinaceous matrix that protects the spores from the sporicide. The normally white ceramic cylinders acquire beige to tan color with some having brown areas due to heavier deposition.

Samples of the prepared ceramic cylinders where obtained from MicroChem laboratory Inc. of Euless, Tex.

The ceramic cylinders and whey protein were used to determine oxidizing activity of various organic acyl polyoxychlorine compounds and formulations. Stability of the organic acyl polyoxychlorine compounds was evaluated using various pH buffers and solution pH.

$Na_2HPO_4$ Buffered Organic Acyl Polyoxychlorine

To a 250 ml Erlenmeyer flask, 190 ml of water was added along with a 1 inch Teflon coated magnetic stirring rod. 5.25 gm sodium chlorate was added and mixed until dissolved. 10.43 gm of sodium phosphate dibasic was added and mixed until dispersed resulting in a slightly hazy solution. 5 ml of acetic anhydride was added and allowed to mix for 35 minutes. The resulting pH was 5.45.

A 5 ml sample was decanted and a scoop of whey protein was added to the sample and swirled. No reaction was detected. 1 ml of 10 wt % sodium bicarbonate was added to the sample and swirled resulting in rapid evolution of gas and formation of foam.

2.5 gms of sodium phosphate dibasic was added to the remaining solution in the Erlenmeyer flask and mixed. The resulting pH was 5.73.

A 5 ml sample was decanted and a scoop of whey protein was added to the sample and swirled. No reaction was detected. 1 ml of 10 wt % sodium bicarbonate was added to the sample and swirled resulting in rapid evolution of gas and formation of foam.

The Erlenmeyer flask was covered with plastic wrap and stored for 10 days. A 5 ml sample was decanted and a scoop of whey protein was added to the sample and swirled. No reaction was detected. 1 ml of 10 wt % sodium bicarbonate was added to the sample and swirled resulting in rapid evolution of gas and formation of foam.

These test illustrate the organic acyl polyoxychlorine demonstrates excellent stability at near neutral pH.

The results illustrate that organic acyl polyoxychlorine solutions can be buffered to higher pH while retaining activity. Initial stability testing illustrates greater stability at higher pH than reported peracetic acid solutions. This can be of significant benefit in applications where strongly acidic pH can induce corrosion or require additional pH buffering prior to or during use.

Ethanolamine pH Buffered Organic Acyl Polyoxychlorine

To a 250 ml Erlenmeyer flask, 190 ml of water was added along with a 1 inch Teflon coated magnetic stirring rod. 5 gm sodium chlorate was added and mixed until dissolved. 5 ml of acetic anhydride was added and allowed to mix for 30 minutes.

A 3 ml Ethanolamine were added and mixed for 10 minutes. The resulting pH was 5.07.

A 10 ml sample was decanted into a vial and 1 ml of 10 wt % sodium bicarbonate was added and swirled. A scoop of whey protein was added to the sample and swirled resulting in rapid evolution of gas and formation of foam.

Organic Acyl Polyoxychlorine from TAED Under Alkaline Conditions

To a 250 ml Erlenmeyer flask, 100 ml of water was added along with a 1 inch Teflon coated magnetic stirring rod. 3 gm sodium chlorate was added and mixed until dissolved. 1 gm sodium carbonate was added while mixing. Then 1.5 gm TAED was added and allowed to mix for 30 minutes. The mixer was turned off and allowed time for the suspended solids to settle. A 10 ml sample was decanted into a vial. A 10 wt % HCl solution was added drop wise until the solution pH was 5.8. A ceramic cylinder was added resulting in rapid evolution of gas across the entire surface of the cylinder.

The results illustrate that organic acyl polyoxychlorine compounds can be produced under alkaline pH conditions. This example leads to the potential of generating organic acyl polyoxychlorine in-situ in applications such as laundry or alkaline pH cooling water biocide treatment.

Bicarbonate Activation of Organic Acyl Polyoxychlorine

To a 250 ml Erlenmeyer flask, 190 ml of water was added along with a 1 inch Teflon coated magnetic stirring rod. 5.25 gm sodium chlorate was added and mixed until dissolved. 13 gm of sodium phosphate dibasic was added and mixed until dispersed resulting in a slightly hazy solution. 5 ml of acetic anhydride was added and allowed to mix for 30 minutes. The resulting pH was approximately 5.7.

A 10 ml sample was treated with 1 ml of 10 wt % sodium bicarbonate solution. This was calculated to be enough to activate approximately 40% of the acetyl chlorate. The ph was 5.7. A ceramic cylinder was added and gas evolution occurred across the entire surface of the cylinder. After approximately 15 minutes the gas evolution diminished.

Once the gas evolution stopped, 1 ml of 10 wt % sodium bicarbonate was added and swirled resuming evolution of gas from the entire surface of the ceramic cylinder.

Results of this test demonstrate the effect of carbon dioxide based alkalinity has on the activation of organic acyl polyoxychlorine as a bleaching agent and oxidizer. With neutralization of excess acidity, bicarbonate and carbonate based alkalinity are converted to carbon dioxide and/or carbonic acid which is readily released as carbon dioxide with agitation. This can be of benefit in applications where bleaching and oxidation are required to remove stains and deposits, but a reservoir of biocide activity is needed to inactivate microbiological organisms. One non-limiting example is a formulation comprising organic acyl polyoxychlorine for use as a cold water sterilant for sterilization of medical equipment such as endoscopes. The activation of a portion of organic acyl polyoxychlorine using bicarbonate or carbonate anions enhances the bleaching and decomposition of the protein and organic matrix that traps the spores onto the ceramic cylinder used in the AOAC 966.04 test. Once the organic matrix is decomposed and dispersed, the spores are in suspension. The suspended spores can then be more easily treated utilizing a reservoir of organic acyl polyoxychlorine. Addition of germinants, surfactants and solvents can function as adjuvants to further enhance the inactivation rate.

Benzoyl Chlorate Generation in DMSO

To a 125 ml Erlenmeyer flask, 50 ml of DMSO was added along with a 1 inch Teflon coated magnetic stirring rod. 2.6 gm sodium chlorate was added and mixed until dissolved. 2.6 gm of benzoic anhydride was added and mixed for 30 minutes. 10 ml of solution was added to 100 ml of distilled water and mixed. The pH of the resulting solution was 3.43.

A 10 ml sample was added to a vial and 1 ml of 10 wt % sodium bicarbonate was added and swirled. A scoop of whey protein was added and swirled resulting in effervescing gas.

A 10 ml sample was added to a vial and 1 ml of 10 wt % sodium bicarbonate was added and swirled. A ceramic cylinder was added resulting in fine gas evolution across the surface of the cylinder.

Results illustrate the ability to produce organic acyl polyoxychlorine compounds from organic carboxylic acid and carboxylic acid derivatives having limited solubility in water using solvents.

Organic Acyl Polyoxychlorine $PO_4$ Buffered w/$HCO_3$

To a 30 ml vial, 18 ml of distilled water was added followed by 2 gm trisodium phosphate and then mixed until dissolved.

To a 250 ml Erlenmeyer flask, 190 ml of water was added along with a 1 inch Teflon coated magnetic stirring rod. 5 gm sodium chlorate was added and mixed until dissolved. 5 ml of acetic anhydride was added and allowed to mix for 30 minutes resulting in stock solution of acetyl chlorate.

A sample comprising 10 ml of stock solution was treated with 12 ml of trisodium phosphate buffer solution and mixed, resulting in a pH of 6.59.

A 5 gm sample of the phosphate buffered stock solution was added to a vial into which a ceramic cylinder was added. No reaction was observed.

A 5 gm sample of the phosphate buffered stock solution was added to a vial. 2 ml of 10 wt % sodium bicarbonate was added and swirled resulting in a pH of 6.79. A ceramic cylinder was added resulting in rapid and sustained evolution of gas across the surface of the cylinder.

Organic Acyl Polyoxychlorine vs PAA with $Ag^+$

A solution of acidified silver chloride was produced by adding 0.01 gm silver chloride to 5 ml of 10 wt % HCl and swirled periodically until dissolved.

Stock solution of 5 wt % $H_2O_2$ was prepared from 70 wt % $H_2O_2$ and distilled water.

Stock solution of 5 wt % Peracetic acid was prepared by reacting acetic anhydride with 70 wt % $H_2O_2$.

Stock solution of 5 wt % acetyl chlorate was prepared by reacting sodium chlorate with acetic anhydride.

10 ml sample of each stock solution were added to glass vials. 100 microliters of acidified silver chloride were added to each, followed by addition of a ceramic cylinder.

Sample #1 comprising hydrogen peroxide showed slow formation of gas on the test cylinder.

Sample #2 comprising the peracetic acid showed rapid gas formation on the test cylinder that was quickly reformed after swirling the sample to remove the accumulated gas.

Sample #3 comprising acetyl chlorate showed no gas formation.

Results illustrate the organic acyl polyoxychlorine demonstrates excellent stability in the presence of catalyst that decompose hydrogen peroxide and peracetic acid.

Acetyl Chlorate with Potassium Monopersulfate

To a 250 ml Erlenmeyer flask, 190 ml of water was added along with a 1 inch Teflon coated magnetic stirring rod. 6.23 gm sodium chlorate was added and mixed until dissolved. 6 ml of acetic anhydride was added and allowed to mix for 30 minutes resulting in stock solution of acetyl chlorate.

100 ml of acetyl chlorate solution was added to an Erlenmeyer flask into which 1.50 gm potassium monopersulfate (PMPS) was added and mixed for 30 minutes.

3-10 ml samples of acetyl chlorate with PMPS was added to 3-glass vials.

Sample 1 was treated with 1.5 ml of 10% sodium bicarbonate. A ceramic cylinder was added demonstrating excellent sustained gas evolution.

Sample 2 was treated with 2.5 ml of 10% sodium bicarbonate. A ceramic cylinder was added demonstrating excellent sustained gas evolution.

Sample 3 was treated with 2.5 ml of 10% sodium bicarbonate. A scoop of whey protein was added demonstrating rapid decomposition.

Sample 4 was treated with 2.5 ml of 10% sodium bicarbonate and stored for 18 hours. A ceramic cylinder was added demonstrating sustained gas evolution but less aggressive than freshly prepared sample #2.

Stabilized Alkaline pH Acetyl Chlorate

To 100 ml distilled water, 3.26 grams KOH was added and mixed until dissolved. 2.20 grams $NaClO_3$ was added and mixed until dissolved. 2.0 ml acetic anhydride was added and allowed to react for 20 minutes. The pH was tested after several minutes and adjusted with KOH or HCl to keep the pH at approximately 9.5. The final pH was 9.61.

10 ml sample was treated with 1 ml of saturated NaHCO3 solution. A ceramic cylinder was added and drops of HCl solution were added reducing the pH to 5.5. The ceramic cylinder rapidly released gas that was sustained for greater than 10 minutes.

After 72 hours, a 10 ml sample was treated with 1 ml of saturated $NaHCO_3$ solution. A ceramic cylinder was added and drops of HCl solution were added reducing the pH to 6.0. The ceramic cylinder rapidly released gas that was sustained for greater than 10 minutes.

After 14 days, a 10 ml sample was treated with 1 ml of saturated $NaHCO_3$ solution. A ceramic cylinder was added and drops of HCl solution were added reducing the pH to approximately 6.0. The ceramic cylinder rapidly released gas that was sustained for greater than 10 minutes. Another 10 ml sample was treated with 1 ml of saturated $NaHCO_3$ solution. An HCl solution were added reducing the pH to approximately 6.0. A scoop of whey was added and swirled resulting in rapid release of gas and decomposition of the whey.

After 21 days, a 10 ml sample was treated with 1 ml of saturated $NaHCO_3$ solution. A ceramic cylinder was added and drops of HCl solution were added reducing the pH to approximately 6.0. The ceramic cylinder rapidly released gas that was sustained for greater than 10 minutes. Another 10 ml sample was treated with 1 ml of saturated $NaHCO_3$ solution. An HCl solution were added reducing the pH to approximately 6.0. A scoop of whey was added and swirled resulting in rapid release of gas and decomposition of the whey.

Results of these tests demonstrate the excellent pH stability of the organic acyl polyoxychlorine compounds.

To a 250 ml Erlenmeyer flask, 50 ml of water was added along with a 1 inch Teflon coated magnetic stirring rod. While mixing, 25 grams of sodium chlorate was added and mixed until dissolved. 25 ml of acetic anhydride was added and allowed to mix for 30 minutes. The otherwise clear solution turned yellow. When mixing was stopped, an oily layer quickly formed on top of the water. Addition of 5 ml of Dowfax C10L combined with 15 minutes of mixing resulted in the formation of an emulsion. Without being bound to a specific theory, it is believed the oil phase was the result of formation of high concentrations of acetyl chlorate. The addition of the chlorate at the acyl carbon reduces the charge density of the molecule, resulting in lower solubility than acetic acid.

Biocide Efficacy of Organic Acyl Polyoxychlorine

Preparation of Bacterial Culture:

From stock culture of *S. aureus* (*Staphylococcus aureus* ATCC#6538) a loopful of stock culture was added to a test tube containing 10 ml nutrient broth and incubated at 35±2° C. for 24±8 hours. After incubation 0.1 ml of the culture was transferred into fresh 10 ml of NB and incubated again at 35±2° C. for 24±8 hours.

Preparation of Disinfectants:

The disinfectant solutions (B and C) and penetrating agent (1) were shaken to re-suspend any particles that might have fallen out of solution. The disinfectant solution was combined with penetrator in a 1:1 ratio of disinfectant to penetrator. The 1:1 ratio was used to make "B:1" and "C:1" disinfectant formulations for use in the test. Also the disinfectant solution was combined with sterile deionized water in a ratio of 1:1 to make "B:DIW" and "C:DIW". All formulas were made within twenty minutes of being used in the test.

Test Procedures:

Nine (9) ml of test disinfectant were placed into sterile 25×150 mm capped test tubes and allowed to come to temperature in a water bath at 20±1° C. One (1.0) ml of the *S. aureus* culture was added to the test tube containing the disinfectant and mixed. After 1.0, 2.0, 3.0, and 5.0 minutes of exposure at 20±1° C., 1.0 ml was removed from the reaction tube and added into 9 ml neutralizing recovery medium (DE). Further serial ten-fold dilutions were made as 1.0 ml into 9 ml portions of NB. One half (0.5) ml portions of all the NB dilutions were transferred onto the surface of nutrient agar (NA) in petri plates. The test tube with DE was filtered through a 0.45 μm membrane filter and the filter was placed onto the surface of NA in a petri plate. The tubes and plates were incubated at 35±2° C. for ≥48 hours. Colonies were counted and multiplied by appropriate dilution factors to determine the number of surviving colony forming units (CFU) of *S. aureus* remaining in the reaction tube at each time point. All four disinfectant solutions were tested in this manner.

The number of surviving colony forming units of *S. aureus* after exposure to various formulations comprising organic acyl polyoxychlorine compounds at 20±° C.

TABLE 1

| Test Chemistry | Exposure Time (min) | Surviving CFU | Log₁₀ Reduction |
|---|---|---|---|
| C: DIW (pH 1.97) | 1 | 7.6 × 10⁶ | 1.05 |
|  | 2 | 7.2 × 10⁶ | 1.08 |
|  | 3 | 4.1 × 10⁶ | 1.32 |
|  | 5 | 2.2 × 10⁶ | 1.59 |
| C: 1 (pH 1.65) | 1 | 40 | 6.33 |
|  | 2 | 18 | 6.68 |
|  | 3 | 7 | 7.09 |
|  | 5 | 3 | 7.46 |
| B: DIW (pH 1.81) | 1 | 0 | 7.85 |
|  | 2 | 0 | 7.85 |
|  | 3 | 0 | 7.85 |
|  | 5 | 0 | 7.85 |
| B: 1 (pH 1.64) | 1 | 0 | 7.85 |
|  | 2 | 0 | 7.85 |
|  | 3 | 0 | 7.85 |
|  | 5 | 0 | 7.85 |

| Reagent | A | B | C |
|---|---|---|---|
| Water | 460 ml | 460 ml | 460 ml |
| NaClO3 | 20 gm | 20 gm | 20 gm |
| Acetic Anhydride | 20 ml | Na | Na |
| 2-Furoic Acid | na | 20 gm | Na |
| Glycolic Acid | na | Na | 20 gm |

| Reagent | #1 |
|---|---|
| Water | 924 ml |
| Dowfax C10L (45 wt %) | 20 ml |
| Tergitol TMN3 (100 wt %) | 1 ml |
| Tergitol TMN6 (90 wt %) | 10 ml |
| Na Dodecylbenzene sulfonate (80 wt %) | 10 gm |
| HEDP (Dequest 2016DG) | 10 gm |
| Phosphoric acid (85 wt %) | 25 ml |

Results: The organic acyl polyoxychlorine comprising furoyl chlorate demonstrated excellent biocide efficacy and membrane penetration even without adjuvants such as surfactants to enhance penetration. The heterocyclic "R" group of the furoyl chlorate demonstrates significantly better penetration of the membrane of the organic than the alkyl "R" group of the glycolyl chlorate. The glycolyl chlorate combined with reagents comprising various surfactants demonstrated significant improvements in membrane penetration and subsequent inactivation of the organisms.

The heterocyclic group of the furoyl chlorate and excess charge neutralizing hydronium ions resulted in an improved octanol/water partition coefficient and subsequent lipophilicity. The ability of the furoyl chlorate to permeate the cell membranes accelerated the rate of kill.

Octanoyl Chlorate

Comparative test where conducted to evaluate the biocide performance based on the lipophilicity of the organic acyl polyoxychlorine compounds. The methods for producing the organic acyl polyoxychlorine compounds were previously disclosed. The pH was increased with ammonium hydroxide to replace the hydronium ions, and additional ammonium chloride was added to increase the concentration of ammonium ions. Several different carbon based structures were used to determine the influence on altering the octanol/water partition coefficient and its influence on biocide efficacy, and Tergitol TMN 6 was used as a surfactant in some samples as indicated. The concentration of organic acyl polyoxychlorine compounds were produced to provide an equivalent level of chlorate anion donor. All of the biocide compositions comprised and equivalent 3000 ppm as NaClO₃. The biocide compositions where produced by combining the following reagents:

| | | 220 ml Samples | | | |
|---|---|---|---|---|---|
| Active | ID | TMN 6 (ml) | Active Dosage (ml) | 17.12% NH4Cl (ml) | Distilled H2O (ml) |
| Benzoyl Chlorate | BC5 | na | 16.5 | 9.22 | 194.28 |
| Benzoyl Chlorate | BC10 | na | 16.5 | 18.44 | 185.06 |
| Benzoyl Chlorate | BC15 | na | 16.5 | 27.50 | 176.00 |
| Furoyl Chlorate | FC15 | na | 16.5 | 27.50 | 176.00 |
| Octanoyl Chlorate | OC15 | na | 16.5 | 27.50 | 176.00 |
| Benzoyl Chlorate | BC15TMN | 2.2 | 16.5 | 27.50 | 173.80 |
| Furoyl Chlorate | FC15TMN | 2.2 | 16.5 | 27.50 | 173.80 |
| Octanoyl Chlorate | OC15TMN | 2.2 | 16.5 | 27.50 | 173.80 |

The biocide compositions where test against *Staphylococcus aureus* at 20° C.±1° C. There were 1.24×10⁸ CFU/ml of *S. aureus* in the culture suspension used for this test.

TABLE 2

| | | | Log 10 Reduction | | | |
|---|---|---|---|---|---|---|
| Active | ID | pH | 0.5 min | 1 min | 2 min | 5 min |
| Benzoyl Chlorate | BC5 | 5.85 | 0 | 0 | 0 | 0 |
| Benzoyl Chlorate | BC10 | 6.14 | 0 | 0 | 0 | 0 |
| Benzoyl Chlorate | BC15 | 6.00 | 0 | 0 | 0 | 0 |
| Furoyl Chlorate | FC15 | 6.54 | <1 | <1 | <1 | <1 |
| Octanoyl Chlorate | OC15 | 5.54 | 8 | 8 | 8 | 8 |
| Benzoyl Chlorate | BC15TMN | 6.54 | 0 | 0 | 0 | 0 |
| Furoyl Chlorate | FC15TMN | 6.54 | 0 | 0 | 0 | 0 |
| Octanoyl Chlorate | OC15TMN | 6.26 | <1 | <1 | <1 | <1 |

As the pH increases, the concentration of hydronium ions decreases resulting in increased influence of the polar charge of the organic acyl polyoxychlorine. However, with an increase in the number of carbons comprising the (R) group, the lipophilicity is increased, resulting in increased biocide efficacy even as the pH rises. Octanoyl chlorate demonstrated an 8 Log Rate of Kill in 30 seconds or less. However, organic acyl polyoxychlorine compounds possessing lower octanol/water partition coefficients demonstrated lower efficacy and many cases showed no biocide efficacy. Furthermore, the use of Tergitol TMN 6 in this particular application and concentration impeded the ability of the octanoyl chlorate to permeate the membranes of the microbes. The formation of micelles likely decreased the lipophilicity to the biocide composition which substantially reduced the rate at which it could permeate the cell membranes.

Furthermore and of great importance, the data clearly illustrates the difference in the properties and characteristics of the organic acyl polyoxychlorine compounds of the invention as compared to percarboxylic acids, chlorine dioxide, hypochlorites and the like. The aforementioned prior art oxidizers are well established as having biocide efficacy against *S. aureus* at concentrations comparable to or even less than that used in these test. The significance of this is the organic acyl polyoxychlorine does not demonstrate "indiscriminate" oxidation with the lipids comprising the cell membrane. The organic acyl polyoxychlorine compounds impose their biocide efficacy as a result of "intracellular activation". Whether the activating mechanism occurs inside the lipid bilayer, the protein portions of the cellular membrane, and/or within the plasma or organelles of the cell itself is unknown. However, it is clear the organic acyl polyoxychlorine is not reacting and inducing lysis as a result of external interactions with the microbial organisms as occurs with the prior art biocides.

The difference in performance characteristics and functionality clearly highlights the differences between organic polyoxychlorine compounds of the invention and established aforementioned prior art chemistries.

The nucleophilic substitution of the organic acyl donor with a polyoxychlorine anion donor results in the formation of a stable and selective oxidizing composition that dramatically improves the survivability of the biocide composition in the presence of high organic loading. This can be of great benefit in applications exemplified by Food Intervention, treatment of Industrial cooling systems, and where penetration of biofilms organic films is desired.

Bleaching Stains

Two sets of cotton swatches were prepared by soaking two swathes in Tart Cherry Juice and two swatches in Coffee. The cotton swatches where laid out to dry. 800 ml of water was added to a 1000 ml beaker, a magnetic stirring rod was added and the beaker was placed on top of a magnetic stirrer. 75 grams of magnesium perchlorate was added with the stirrer sustaining a vortex approximately ⅔ the distance from the top of the solution to the stifling rod. 75 grams of succinic anhydride was slowly added and allowed to mix until no observable succinic anhydride remained. 75 grams of sodium bicarbonate was slowly added allowing sufficient time for release of carbon dioxide without vigorous gas release and the associated localized increases in pH that can accelerate decomposition of the succinyl perchlorate. The resulting bleach solution was diluted with additional water to obtain 1000 ml of bleach solution.

To a 500 ml beaker, 165 ml of water as measured in a graduated cylinder and added to the beaker. 335 ml of bleach solution was added to obtain 500 ml of diluted bleach solution. This dilution process was repeated with another 500 ml beaker so that two beakers of 500 ml of diluted bleach solution were available.

One of the Tart Cherry Juice stained swatches and one of the coffee stained swatches was added to each of the diluted bleach solutions. The swatches were periodically moved with a Teflon spoon liberating large volumes of gas. After 5 minutes, the swatches where removed from the diluted bleach solutions and added to a washing machine along with a towel to enhanced their movement in the machine. A small amount of surfactant Triton DF-12 from Dow Chemical was added to the machines dispenser. The cycle was set for 55 minutes using hot water wash. After washing the contents were removed from the machine, placed into the drier and dried on high temperature until dried.

The swatches were placed next to the swatches that had not been bleached, as well as a sample of cotton swatch not stained. The bleached samples had been restored to the whiteness of the original cotton swatches. No remaining stain was observed on either the tart cherry juice stained or the coffee stained swatches.

Laundry Bleaching

To 200 ml of water, 10 grams of magnesium perchlorate was added and mixed until dissolved. 10 grams of maleic anhydride was added and mixed until the suspension was completely dissolved. Two white towels stained with dried coffee were added to a front loaded washing machine. The bleach solution was added to the bleach dispenser and Triton DF-12 surfactant was added to the detergent dispenser. The machine was set to wash whites and started. After 55 minutes the towels were removed and dried. The towels were cleaned of the coffee stains. There was no distinguishable difference between the portions of the towels stained with coffee and those that were not.

To 200 ml of water, 10 grams of magnesium perchlorate was added and mixed until dissolved. 10 grams of maleic anhydride was added and mixed until the suspension was completely dissolved. The solution was poured directly onto the front portion of a yellow sweatshirt and was then added into a front loaded washing machine. Liquid Tide laundry detergent was added to the detergent dispenser. The washing machine cycle was set to wash colors. After 31 minutes the sweatshirt was removed and dried. There was no distinguishable difference between the portions of the sweatshirt that was treated with the treated portion and the untreated portion of the sweatshirt. The bleach compositions of the invention demonstrate color-safe characteristics.

Perchlorate Solid Composition

To 100 ml of tap water, 5 grams of magnesium perchlorate was added and mixed, followed by addition of 5 grams of succinic anhydride. The aqueous solution was vigorously mixed until no succinic anhydride was observable in the solution. Approximately 25 ml of solution was stored in a flask and allowed to dry by slowly evaporating the water at atmospheric conditions. The bottom of the flask had a film of crystals having an appearance similar to snowflakes. 25 ml of cold tap water was added and swirled to dissolve the crystals. A 10 ml vial was filled and a small amount of sodium bicarbonate was added and swirled to elevate the pH to over 5.0. Whey protein was added and the vial was swirled. The whey protein rapidly decomposed forming a cloud of gas and formation of foam on the top of the vial.

This test showed that an acidic aqueous solution of succinyl perchlorate is sufficiently stable to form a solid succinyl perchlorate. The solid succinyl perchlorate could be reconstituted to form an aqueous solution while retaining its reactivity toward whey protein.

Organic perchlorates have been known to be explosive in concentrated liquid and solid forms. It may be advantageous to include an additive in liquid solutions sold in the commercial and retail markets that induces decompositions when the organic acyl polyoxychlorine is concentrated, thereby preventing formation of solid crystals. Non-limiting examples of methods that could be used to prevent the concentrating of organic acyl polyoxychlorine compounds could include adding a substance to the aqueous biocide composition that crystallizes when concentrated above its saturation point and functions as a catalyst to initiate decomposition at the acyl polyoxychlorine bond. Yet another example could be a substance that elevates the pH as the solution concentrates, thereby destabilizes the biocide composition and initiating decomposition.

| Perchlorate Test | | | | | |
|---|---|---|---|---|---|
| Sample 100 ml $H_2O$ | Maleic | Acetic | Magnesium Perchlorate | 10 ml vial $NaHCO_3$ | Whey RxN |
| #1 Alkene | 1.0 gram | n/a | 1.0 gram | X | Vigorous |
| #1 Alkyl | n/a | 1.0 gram | 1.0 gram | X | vigorous |

Test were conducted using acetic anhydride and maleic anhydride reacted with magnesium perchlorate. The resulting solution where stable under acidic conditions but reacted vigorously when the pH was buffered using sodium bicarbonate followed by addition of whey protein.

What is claimed is:

1. A method of killing microorganisms comprising the steps of:

forming a biocide composition comprising a carrier and an organic acyl polyoxychlorine having the general formula;

$$R\left[\begin{array}{c} X \\ | \\ C=O \end{array}\right]_n$$

wherein (X) is a polyoxychlorine selected from at least one of a chlorate having the general formula $ClO_3$ and perchlorate having the general formula $ClO_4$, (R) comprises a $C_1$ to $C_{17}$ primary carbon based structure, (n) is one or more; and contacting the microorganisms with the composition, wherein the organic acyl polyoxychlorine experiences intracellular activation releasing oxychlorine intermediates.

2. The method according to claim 1, further comprising controlling food-borne pathogenic bacteria by contacting the biocide composition with the bacteria.

3. The method according to claim 1, further comprising applying the biocide composition for food intervention for the control of food-borne pathogenic bacteria.

4. The method according to claim 1, further comprising applying the biocide composition to hard surfaces.

5. The method according to claim 1, further comprising applying the biocide composition to recirculating systems.

6. The method according to claim 1, wherein the primary carbon backbone (R) comprises an alkyl group.

7. The method according to claim 1, wherein the primary carbon backbone (R) comprises an arylalkyl group.

8. The method according to claim 1, wherein the primary carbon backbone (R) comprises a cycloalkyl group.

9. The method according to claim 1, wherein the primary carbon backbone (R) comprises an aromatic group.

10. The method according to claim 1, wherein the primary carbon backbone (R) comprises a heterocyclic group.

11. The method according to claim 1, wherein the primary carbon backbone (R) comprises at least one $C_1$ to $C_{13}$ alkyl group.

12. The method according to claim 1, wherein the primary carbon backbone (R) comprises at least one $C_7$ to $C_{11}$ alkyl group.

* * * * *